(12) United States Patent
Buller

(10) Patent No.: US 12,076,122 B2
(45) Date of Patent: *Sep. 3, 2024

(54) PACING TEMPLATES FOR PERFORMANCE OPTIMIZATION

(71) Applicant: The Government of the United States, as represented by the Secretary of the Army, Fort Detrick, MD (US)

(72) Inventor: Mark J. Buller, Douglas, MA (US)

(73) Assignee: The Government of the United States, as represented by the Secretary of the Army, Ft. Detrick, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/101,501

(22) Filed: Jan. 25, 2023

(65) Prior Publication Data

US 2023/0165473 A1 Jun. 1, 2023

Related U.S. Application Data

(63) Continuation of application No. 16/091,982, filed as application No. PCT/US2017/027991 on Apr. 17, 2017, now Pat. No. 11,571,134.

(Continued)

(51) Int. Cl.
*A61B 5/11* (2006.01)
*A61B 5/0205* (2006.01)
(Continued)

(52) U.S. Cl.
CPC ...... *A61B 5/02055* (2013.01); *A61B 5/02438* (2013.01); *A61B 5/1118* (2013.01);
(Continued)

(58) Field of Classification Search
CPC ......... A61B 5/01; A61B 5/1118; A61B 5/222; A61B 5/7275; A61B 2562/0271; G16H 50/30
See application file for complete search history.

(56) References Cited

U.S. PATENT DOCUMENTS

| 4,883,063 A | 11/1989 | Bernard et al. |
| 5,441,476 A | 8/1995 | Kitado et al. |

(Continued)

FOREIGN PATENT DOCUMENTS

| CA | 2650576 A1 | 10/2006 |
| FR | 2998158 A1 | 5/2014 |

(Continued)

OTHER PUBLICATIONS

Ozaki, T., et al., "The local linearization filter with application to nonlinear system identifications," Proc. first US/Japan Conf Frontiers Stat Modeling: An Information Approach, Springer, pp. 217-240, 1994.

(Continued)

*Primary Examiner* — Lawrence S Galka
(74) *Attorney, Agent, or Firm* — Leigh Z. Callander

(57) ABSTRACT

A system or a method for providing pacing guidance to an individual for a particular activity based on a physiological strain index (PSI) or an adaptive physiological strain index (aPSI). The system in at least one embodiment includes a heart rate monitor, a memory storing multiple pacing templates, a clock, an activity completion module, an output device, and a processor configured to perform multiple steps resulting in outputting pacing information to the individual. The pacing information selected in at least one embodiment is based on the individual's heart rate that provides in part a PSI or aPSI, the elapsed time for the activity, and the amount of progress through the activity.

20 Claims, 9 Drawing Sheets

Related U.S. Application Data

(60) Provisional application No. 62/323,320, filed on Apr. 15, 2016.

(51) Int. Cl.
  *A61B 5/024* (2006.01)
  *G06F 16/901* (2019.01)
  *G06N 5/022* (2023.01)
  *G06N 20/00* (2019.01)

(52) U.S. Cl.
  CPC ......... *G06F 16/9017* (2019.01); *G06N 5/022* (2013.01); *G06N 20/00* (2019.01)

(56) References Cited

U.S. PATENT DOCUMENTS

| | | |
|---|---|---|
| 7,037,273 B2 | 5/2006 | Zhu et al. |
| 7,251,454 B2 | 7/2007 | White |
| 7,805,186 B2 | 9/2010 | Pulkkinen et al. |
| 7,827,011 B2 | 11/2010 | Devaul et al. |
| 7,883,463 B2 | 2/2011 | Sattler et al. |
| 7,942,825 B2 | 5/2011 | Ranganathan et al. |
| 8,204,786 B2 | 6/2012 | Leboeuf et al. |
| 8,303,172 B2 | 11/2012 | Zei et al. |
| 8,465,397 B2 | 6/2013 | Saalasti et al. |
| 8,936,552 B2 | 1/2015 | Kateraas et al. |
| 9,204,798 B2 | 12/2015 | Proud |
| 9,204,806 B2 | 12/2015 | Stivoric et al. |
| 11,571,134 B2 | 2/2023 | Buller |
| 2002/0009119 A1 | 1/2002 | Matthew et al. |
| 2002/0165443 A1 | 11/2002 | Mori |
| 2004/0034295 A1 | 2/2004 | Salganicoff et al. |
| 2005/0113703 A1 | 5/2005 | Farringdon et al. |
| 2007/0239038 A1 | 10/2007 | Nicolaescu et al. |
| 2007/0295713 A1 | 12/2007 | Carlton-Foss |
| 2008/0224866 A1 | 9/2008 | Rehman |
| 2008/0262320 A1 | 10/2008 | Schaefer et al. |
| 2009/0043176 A1 | 2/2009 | Nakajima et al. |
| 2009/0069642 A1 | 3/2009 | Gao et al. |
| 2009/0069647 A1 | 3/2009 | McNames et al. |
| 2010/0113894 A1 | 5/2010 | Padiy |
| 2010/0280331 A1 | 11/2010 | Kaufman et al. |
| 2011/0004072 A1 | 1/2011 | Fletcher et al. |
| 2011/0144457 A1 | 6/2011 | Coulon |
| 2011/0251495 A1 | 10/2011 | Province et al. |
| 2011/0257542 A1 | 10/2011 | Russell et al. |
| 2011/0288381 A1 | 11/2011 | Bartholomew et al. |
| 2011/0301432 A1 | 12/2011 | Riley et al. |
| 2012/0022336 A1 | 1/2012 | Teixeira et al. |
| 2012/0068848 A1 | 3/2012 | Campbell et al. |
| 2012/0078127 A1 | 3/2012 | McDonald et al. |
| 2012/0197584 A1 | 8/2012 | Coates |
| 2013/0237772 A1 | 9/2013 | Pisani et al. |
| 2013/0345978 A1 | 12/2013 | Lush et al. |
| 2014/0180027 A1 | 6/2014 | Buller |
| 2014/0249434 A1 | 9/2014 | Banet et al. |
| 2014/0343372 A1 | 11/2014 | Ahmed et al. |
| 2014/0357960 A1 | 12/2014 | Phillips et al. |
| 2015/0031964 A1 | 1/2015 | Bly et al. |
| 2015/0106052 A1 | 4/2015 | Balakrishnan et al. |
| 2015/0142332 A1 | 5/2015 | Jeon et al. |
| 2015/0182130 A1 | 7/2015 | Utter |
| 2016/0081629 A1 | 3/2016 | Rostalski et al. |
| 2017/0071477 A1 | 3/2017 | Lin et al. |
| 2017/0238811 A1 | 8/2017 | Buller et al. |

FOREIGN PATENT DOCUMENTS

| | | | |
|---|---|---|---|
| JP | 2005226902 A | | 8/2005 |
| JP | 2009-142333 A | | 7/2009 |
| JP | 2018134137 A | | 8/2018 |
| WO | 88/09146 A1 | | 12/1988 |
| WO | 2009034218 A | | 3/2009 |
| WO | 2011032016 A1 | | 3/2011 |
| WO | 2015185927 A1 | | 12/2015 |
| WO | 2020/180454 A9 | | 9/2020 |

OTHER PUBLICATIONS

Chen, Chi-Tsong, "Linear System Theory and Design," 3rd ed. Oxford, NY: Oxford University Press, 1999, pp. 106-111.

Bulut, Yalcin, et al., "Process and Measurement Noise Estimation for Kalman Filtering," Structural Dynamics, Conf Proc Soc Exp Mech Series 3, pp. 375-386, 2011.

Cuddy, John S. et al., "A reduced core to skin temperature gradient, not a critical core temperature, affects aerobic capacity in the heat," vol. 43, Jul. 2014, pp. 7-12.

Wright-Beatty, Heather E. et al., "Increased air velocity during exercise in the heat leads to equal reductions in hydration shifts and interleukin-6 with age," Jun. 19, 2014, vol. 114, Issue 10, pp. 2081-2092.

Esteve-Lanao, Jonathan, et al., "How Do Humans Control Physiological Strain during Strenuous Endurance Exercise?," PLoS ONE, vol. 3, No. 8, https://doi.org/10.1371/journal.pone.0002943, Aug. 13, 2008, pp. 1-11.

Pokora, Ilona, et al., "Application of A Physiological Strain Index in Evaluating Responses to Exercise Stress—A Comparison Between Endurance and High Intensity Intermittent Trained Athletes," Journal Human Kinetics, vol. 50, Apr. 13, 2016, pp. 103-114.

Wan, Margaret, "Assessment of Occupational Heat Strain," Scholar Commons, Graduate Theses and Dissertations, http://scholarcommons.usf.edu/etd/2745, Jul. 17, 2016, pp. 1-66.

Buller, Mark J., et al., "Real-Time Core Body Temperature Estimation from Heart Rate for First Responders Wearing Different Levels of Personal Protective Equipment," Ergonomics, http://dx.doi.org/10.1080/00140139.2015.1036792, 2015, pp. 1-12.

Gunga, H. C., et al., "The Double Sensor—A Non-Invasive Device to Continuously Monitor Core Temperature in Humans on Earth and in Space," Respiratory Physiology & Neurobiology, Oct. 2009, pp. S63-S68, vol. 169, Supplement.

Potter, Adam W., et al., "Mathematical Prediction of Core Body Temperature from Environment, Activity, and Clothing: The Heat Decision Aid (HSDA)," Journal of Thermal Biology, Jan. 16, 2017, pp. 78-85, vol. 64.

Richmond, Victoria L., et al., "Prediction of Core Body Temperature from Multiple Variables," Ann. Occup. Hyg., Aug. 12, 2015, pp. 1168-1178, vol. 59, No. 9.

Wilkerson, David M., et al., "The Effect of Cool Water Ingestion on Gastrointestinal Pill Temperature," Medicine & Science in Sports & Exercise, 2008, pp. 523-528, vol. 40, No. 3.

United States Patent and Trademark Office, Office Action for U.S. Appl. No. 16/767,970, filed Dec. 10, 2021, pp. 42-48.

Sawka, Michael N., et al., "Intergrated Physiological Mechanisms of Exercise Performance, Adaptation, and Maladaptation to Heat Stress," Comphrensive Physiology, comprehensivephysiology.com, Oct. 2011, pp. 1883-1928, vol. 1.

U.S. Patent and Trademark Office, Office Action in U.S. Appl. No. 16/091,982, filed Jun. 16, 2022, pp. 1-17.

Al-Mukhaizeem, F., et al., "Comparison of temporal artery, rectal and esophageal core temperature in children: results of pilot study", Pediatric Child Health, Sep. 2004, pp. 461-465, vol. 9.

Bland, J. and Altman, D., "Statistical methods for assessing agreement between two methods of clinical measurements," Lancet, 1986, pp. 307-310, vol. 1.

Brauer, A., et al., "Determination of core body temperature. A comparison of esophogeal, bladder and rectal temperature: A comparison of esophageal, bladder and rectal temperature during postoperative rewarming" (translated title), Der Anaesthesist, Fall 1997, pp. 683-688, vol. 46.

Buller, MJ et al., "Thermal work strain during Marine rifle squad operations in Afghanistan (Mar. 2010)," USARIEM Technical Report No. T11-02 (AD A501301), Mar. 2010, pp. 1-39.

Buller, Mark J, et al. "Estimation of Human Internal Temperature from Wearable Physiological Sensors." IAAI. 2010.

(56) References Cited

OTHER PUBLICATIONS

Buller, M.J. et al.; "Human thermoregulatory system state estimation using non-invasive physiological sensors," in Engineering in Medicine and Biology Society, EMBC, 2011 Annual International Conference of the IEEE, vol. No., pp. 3290-3293, Aug. 30, 2011-Sep. 3, 2011.

Buller, M.J. et al., "Estimation of human core temperature from sequential heart rate observations," Physiological Measurement, 2013, pp. 781-798, vol. 34.

Byrne, C. and Lim, C.L., "The ingestible telemetric body core temperature sensor: a review of validity and exercise applications," Br. J. Sport Med., 2007, pp. 126-133, vol. 41.

Cheuvront, Samuel et al., "Evaluation of the limits to accurate sweat loss prediction during prolonged exercise," Eur. J. Appl. Physiol., 2007, pp. 215-224, vol. 101.

Cuddy, JS et al., abstract for "Skin temperature and heart rate can be used to estimate physiological strain during exercise in the heart in a cohort of fit and unfit males," Association of Military Surgeons of the U.S., Mil Med., Jul. 2013.

Degroot, David W. et al., "Prediction Models for Core Temperature During Heat Stress Vary with Exercise Intensity," Medicine & Science in Sports & Exercise, May 2007, p. S436, vol. 39, issue 5.

DeGroot, David W. et al., "Validation of the ICDA model for predicting body core temperature," Medical & Science in Sports & Exercise, May 2008, p. S367, vol. 40, issue S.

Fiala, Dusan et al., "Computer prediction of human thermoregulatory and temperature responses to a wide range of environmental conditions," International Journal Biometeorol, 2001, pp. 143-159, vol. 45.

Fick, Adolph, "On liquid diffusions," Journal of Membrane Science, 1995, pp. 30-39, vol. 10.

Fox, R.H. et al., "A new method for monitoring deep body temperature from the skin surface," Clinical Science, 1973, pp. 81-86, vol. 44.

Frank, A. et al., "The cumulative heat strain index—a novel approach to assess the physiological strain induced by exercise heat stress," Eur. J. Appl. Physiol., 2001, pp. 527-532, vol. 84.

Grubbs, Frank E., "Procedures for detecting outlying observations in samples," AD-781 499, BRL Report No. 1713, Apr. 1974, pp. 1-53.

Gunga, Hanns-Christian et al., "A non-invasive device to continuously determine heat strain in humans," Journal of Thermal Biology, 2008, pp. 297-307, vol. 33.

Gunga, H.C., et al., "The double sensor—a non invasive device to continuously monitor core temperature in humans on earth and in space," Respir. Physiol, Neurobiology, 2009, pp. S63-S68, vol. 169S.

Havenith, George, "Individualized model of human thermoregulation for the simulation of heat stress response," J. Appl. Physiol., 2001, pp. 1943-1954, vol. 90.

Sargent II, Frederick et al., "Physiological variability in young men," Physiological Measurements of Metabolic Functions, ed. CF Consolazio, RE Johnson and LJ Pecora, 1963, pp. 453-480, New York: McGraw-Hill.

Kalman, R.E., "A New Approach to Linear Filtering and Prediction Problems," Journal of Basic Engineering, Mar. 1960, pp. 35-45, vol. 82.

Karp, Jason R., "Heart Rate Training for Improved Running Performance," www.coachr.org/heart_rate_training_for_improvement. htm., printed on Mar. 29, 2016.

Kenefick, Robert W. et al., "DEET insect repellent: effects on thermoregulatory sweating and physiological strain," Eur. J. Appl. Physiol., 2011, pp. 3061-3068, vol. 111.

Kraning, Kenneth K., "A mechanistic computer simulation of human work in heat that account for physical and physiological effects of clothing, aerobic fitness and progressive dehydration," Journal of Thermal Biology, 1997, pp. 331-342, vol. 22, No. 415.

Latzka, William A. et al., "Hyperhydration: thermoregualtory effects during compensable exercise heat stress," J. Appl. Physiol., 1997, pp. 860-866, vol. 83.

Latzka, William A. et al., "Hyperhydration: tolerance and cardiovascular effects during uncompensible exercise heat stress," J. Appl. Physiol., 1998, pp. 1858-1864, vol. 84.

Lee, Jason K.W. et al., "Thermoregulation, pacing and fluid balance during mass participation distance running in a warm and humid environment," Eur. Jour. Appl. Physiol., 2010, pp. 887-898, vol. 109.

Lefrant, J.Y. et al., "Temperature measurement in intensive care patients: comparison of urinary bladder, pesophageal, rectal, axillary, and inguinal methods versus pulmonary artery core method," Intensive Care Med., 2003, pp. 414-418, vol. 29.

Lim, Chin Leong et al., "Human Thermoregulation and Measurement of Body Temperature in Exercise and Clinical Settings," Annals Academy of Medicine, Apr. 2008, pp. 47-53, vol. 37, Singapore.

Montain, Scott J. et al., "Influence of graded dehydration on hyperthermia and cardiovascular drift during exercise," J. Appl. Physiol., 1992, pp. 1340-1350, vol. 73.

Moran, Daniel S. et al., "A physiological strain index to evaluate heat stress," American Journal of Physiological Regulation Integr. Comp. Physiol., 1998, pp. R129-R134, vol. 275.

Niedermann, Reto et al., "Prediction of human core body temperature using non-invasive measurement methods," International Journal of Biometeorology, published online Jun. 13, 2013, pp. 1-9.

Orderud, Fredrik, "Comparison of Kalman Filter Estimation Approaches for State Space Models with Nonlinear Measurements," In. Proc. of Scandinavian Conference on Simulation and Modeling, pp. 1-8, 2005.

Sawka, Michael N. et al., "Chapter 26 Physiological Systems and Their Responses to Conditions of Heat and Cold," ACSM's Advanced Exercise Physiology, ed. CM Tipton, MN Sawka, CA Tate, and RL Terjung, pp. 535-563, Williams & Wilkins, New York.

Steck, Luke N. et al., "Non-invasive measurement of the human core temperature," International Journal of Heat and Mass Transfer, 2011, pp. 975-982, vol. 54.

Teunissen, LPJ et al., "Non-invasive continuous core temperature measurement by zero heat flux," Physiological Measurement, 2011, pp. 559-570, vol. 32.

Welch, Greg et al., "An introduction to the Kalman Filter," Technical Report TR 95-041, Department of Computer Science, 2001, pp. 19-29, University of North Carolina at Chapel Hill, NC.

Yamakage, Michiaki et al., "Evaluation of newly developed monitor of deep body temperature," Journal of Anesthesia, 2002, pp. 354-357, vol. 16.

Yokota, Miyo et al., "Thermoregulatory model to predict physiological status from ambient environment and heart fate," Computers in Biology Medicine and Medicine, 2008, pp. 1187-1193, vol. 38.

Espacenet, English abstract for FR2998158 A1, printed on Mar. 21, 2016.

Espacenet, English abstract for JP2005226902 A, printed on Mar. 21, 2016.

Buller, Mark J. "Human Thermal-Work Strain Performance Optimization from Wearable Physiological Sensors." Dec. 31, 2015. https://cs.brown.edu/research/pubs/theses/phd/2015/buller.pdf, pp. 1-193.

Baratchi, Mitra, et al., "Towards Decisive Garments for Heat Stress Risk Detection," UBICOMP/ISWC '16 Adjunct, Sep. 12-16, 2016, pp. 1-6.

Richmond, Victoria L., et al., "Prediction of Core Body Temperature from Multiple Variables," The Annuals of Occupational Hygiene, 2015, pp. 1-11.

Seng, Kok-Yong, et al., "Nonlinear mixed effects modelling for the analysis of longitudinal body core temperature data In healthy volunteers," Physiological Measurement, vol. 37, Mar. 10, 2016, pp. 485-502.

U.S. Patent and Trademark Office, PCT Application No. PCT/US2017/027791, International Search Report, Jun. 29, 2017.

U.S. Patent and Trademark Office, PCT Application No. PCT/US2017/027791, Written Opinion, Jun. 29, 2017.

European Patent Office, English abstract for JP2018134137A, printed on Apr. 28, 2023.

PACING TEMPLATES FOR PERFORMANCE OPTIMIZATION

This patent application is a continuation application of U.S. patent application Ser. No. 16/091,982, filed on Oct. 9, 2018, which was a 371 National Stage application from International Application No. PCT/US2017/027991, filed on Apr. 17, 2017, which claims priority to and the benefit of U.S. Patent Application No. 62/323,320 filed on Apr. 15, 2016, which is hereby incorporated by reference.

I. FIELD OF THE INVENTION

The invention in at least one embodiment relates to a method and/or system for determining a real-time pacing schedule for an individual using their physiological strain state (PSS) (determine by sensors or other means), the completion state of their task (determined by sensors or other means), and a pacing template (selected from a set of templates). In a further embodiment, the pacing template is optimized for the individual's task, environmental conditions, and/or the clothing worn by the individual.

II. BACKGROUND OF THE INVENTION

Heat illness is a risk to people in occupations where there are heavy workloads, hot environments, or where there is the use of protective clothing or equipment. Athletes must often compete with very high work rates in extremes of temperature. Miners and steelworkers can have very hot work environments. Firefighters, tactical law enforcement, first responders, and military must often wear personal protective equipment (PPE) to protect them from the threat of fire, chemical, biological, nuclear, or explosive agents or devices.

While these PPE ensembles offer the individual protection, they limit one's ability to thermoregulate (Muza, Banderet and Cadarette 2001, Givoni and Goldman, 1972). With reduced vapor permeability, these PPE ensembles limit evaporative heat transfer from the body to the environment. In addition, the added insulative properties of these ensembles further decreases the rate heat can transfer to the environment by conductive and convective routes. Thus, even in temperate conditions, the rate of metabolic heat produced from physical work can often exceed the rate at which heat can be transferred to the environment. In these situations, first responders' core body temperatures will continue to rise while working. If this heat strain is not effectively managed, it can lead to heat exhaustion, collapse, or even death from heat stroke (Bouchama and Knochel 2002). These, heat strain risks can be accentuated in a team setting by the psychological pressure to continue working even if an individual is aware of feeling ill (Porter 2000).

The military often form an extreme example where they combine high work rates, wear protective clothing and equipment, and often have to work in extremes of climate. Steinman (1987), in his historical review of the effects of heat on military operations, cites cases where heat illness played a significant degrading effect, including examples from the Roman army (Jarcho 1967), the European Crusaders in the middle-ages (Lindsay 1936), Napoleon (Dible 1970), the British Army in India in the 19th Century (Parkes 1864), and the First World War (Wilcox 1920). From 2008 to 2012, there were over 13,000 incidents of heat illness events in the U.S. Military (MSMR 2013), including 1,867 cases of heat stroke.

The National Fire Protection Agency has tracked firefighter fatalities in the U.S. for many years and finds that over the ten year period 2001-2010, heat stroke accounts for 5% of firefighter fatalities during training (Fahy 2012). Further, Karter and Molis (2014) identify that thermal stress accounts for 3% of 2013 firefighter injuries (over 2000 incidents). But this does not capture the full effect of thermal-work strain. The leading cause of firefighter deaths in the U.S. is myocardial infarction (~38%) (Fahy et al., 2006, 2013). In their analysis, Fahy et al. (2012) cite that the additional strain imposed by the high work demands of firefighting is likely a contributing factor to cardiac arrest. In these circumstances, the cardiovascular system is stressed from the competing needs of thermoregulation and metabolic requirements (Smith et al., 2001).

For other occupations, the U.S. Occupational Safety and Health Administration (OSHA) specifically records heat fatalities for their covered industries. Their map shows fatalities in most regions of the U.S. (OSHA Heat Fatalities Map, https://ww.osha.gov/SLTC/heatillness/map.html (accessed Feb. 1, 2015)), and they document over 100 fatalities from 2008 to 2014 (OSHA Heat Fatalities, http://www.osha.gov/SLTC/heatillness/map_text (accessed Feb. 1, 2015)).

Additionally, heat illness may be a contributing factor in other workplace accidents. While heat exhaustion can lead to dizziness and fainting (Bouchama and Knochel, 2002), there is some evidence that hyperthermia can degrade working memory (Stubblefield et al., 2006) and also decrease our ability to detect changes in the surrounding environment (Sun et al., 2011). These additional effects could easily be contributing factors for other physical workplace injuries.

Efforts to identify and control the incidence of heat illness or injury originally focused on identifying high-risk environments and providing guidance for acceptable work/rest schedules (Yaglow and Minard, 1956, 1957; OSHA 1985; NIOSH 1986). Risk of heat illness can be reduced by acclimation, appropriate work/rest schedules, and proper hydration (Minard, 1961). However, assessing risk of heat stress from environmental conditions alone fails to account for individual differences, such as acclimation status, fitness, body composition and morphology, and prior heat injury, which can play important roles in an individual's response to working in hot environments (Kark et al., 1996; Carter et al., 2005). A study of US military heat stroke training deaths during "World War II" found that most "fatalities associated with heavy exercise occur at relatively low temperatures, when the total heat stress is commonly underestimated." (Schickele 1947). Similarly, recent work by Owen, Leon, and McKinnon (2013) found that ~35% of heat stroke cases in the U.S. military from 2000-2007 occurred in low risk individuals who were "practicing sound heat mitigation strategies." Abriat et al. (2014) have similar findings, where out of 182 cases of heat stroke, 19% occurred where the environmental temperature was less than 15° C. The major contributing factor over all the cases was individual motivation to complete the task. This is a common theme in team settings, where an individual may be feeling unwell but does not want to let down his/her other team members. Lui et al. (2014) detail two examples where very experienced wildland firefighters succumbed to heat stroke even though they maintained proper hydration.

It is not only the acute problem of heat illness that needs to be solved. Over the long run, thermal-work strain has a degrading effect upon performance (Cheuvront et al., 2010). Successive bouts of thermally-stressful work appear to have a cumulative effect on the thermal-work strain of the individual (Horn et al., 2013). The critical nature of effectively managing thermal-work strain over time is crystallized in the recent Ebola virus treatment centers. Here, Chertow et al.

(2014) detail that physicians were only able to spend 45 to 60 minutes, two or three times per day, in direct contact with their patients because of the "substantial heat exposure and fluid losses". Roberts and Perner (2014) suggest more time-intensive care for Ebola virus patients was not available in part because of the limited time available to health workers when in personal protective gear.

Finally, while thermal-work strain may affect the performance or safety of the individual, the team perspective also needs to be considered. A team member not able to do his/her part means other team members must step in, which makes the whole team work harder. If an individual collapses from heat illness, this medical event is of concern to the whole team. Now one or more team members have to stop what they are doing and assist the individual with hyperthermia. This can be especially problematic for teams working in hazardous environments, where the team member has to be carefully extracted from a contaminated area.

III. SUMMARY OF THE INVENTION

Hot environments pose a risk of heat illness for many emergency workers, athletes, and other professions especially when heavy workloads or protective clothing are necessary. Modern wearable physiological monitors may be able to mitigate risk of heat illness and improve performance if they are able to track health state and provide feedback to the user. However, effective algorithms and models to make use of wearable sensor information are lacking. Two contributions include: 1) a method for health state estimation of the latent human body core temperature from physiological sensors, and 2) models for policy estimation to provide automated advice to reduce thermal-work strain and improve physiological performance over a course of prescribed work.

Continuous measurement of body core temperature, a requisite of thermal-work strain health state, has been an open physiology problem in the field. The physiological dependencies of the human thermo-regulatory system can be cast into a dynamic Bayesian network model that allows us to estimate body core temperature from wearable physiological sensors. This model was effectively simplified to use only an input of heart rate which is collected by many commercial wearable sensor systems. This approach is validated across different combinations of temperature, hydration, clothing, and acclimation states, and shows similar comparison accuracy to accepted laboratory measures. The use and effectiveness of the algorithm from experimental trials was demonstrated during a first responder live training event.

A Markov decision process that uses health state estimates to optimize individual pacing strategies to reduce the overall level of thermal-work strain is presented. The estimation of real world activity objectives and thermal-work strain constraints as a reinforcement learning problem described. Using a dynamical simulation of physiology, pacing estimates from this model are shown to reduce overall thermal-work strain.

The health state and policy estimation contributions were evaluated in the context of an implementation to compare human self-guided pace and policy guided pace. The results show that the policy allowed individuals to complete the task with meaningfully lower thermal-work strain. Real-time feedback from the model was demonstrated to match the thermo-regulatory efficiency of a well-trained athlete.

In at least one embodiment, a system for providing pacing guidance to an individual includes: a heart rate monitor; a memory storing a plurality of pacing templates configured for the activity being performed by the individual and a look-up table having entries for the plurality of pacing templates; a clock; an activity completion module; an output device; a processor in communication with the heart rate monitor, the memory, the clock, the activity completion module, and the output device, the processor configured to receive a heart rate signal from the heart rate monitor, receive a time from the clock, receive a signal from the activity completion module representing an amount of the activity completed by the individual, calculate a physiological strain index (PSI) from the heart rate signal, selecting one pacing template based on the PSI, the time, the amount of the activity completed using the look-up table in the memory, and outputting information in the pacing template to the output device.

Further to the previous embodiment, the heart rate monitor is selected from a group consisting of a heart rate sensor attached to the subject person, a processor for receiving EKG signals from electrodes attached to the person, a pulse oximeter sensor, or a processor for receiving a ballistic-cardiogram signal.

In at least one embodiment, a system for providing pacing guidance to an individual, the system including: a heart rate monitor; a memory storing a plurality of pacing templates configured for the activity being performed by the individual and a look-up table having entries for the plurality of pacing templates; an activity completion module; an output device; a processor in communication with the heart rate monitor, the memory, the clock, the activity completion module, and the output device, the processor configured to receive a heart rate signal from the heart rate monitor, receive a signal from the activity completion module representing an amount of the activity completed by the individual, calculate a physiological strain index (PSI) from the heart rate signal, selecting one pacing template based on the PSI and the amount of the activity completed using the look-up table in the memory, and outputting information in the pacing template to the output device.

In at least one embodiment, a system for providing pacing guidance to an individual, the system includes: a physiological strain state (PSS) module; a memory storing a plurality of pacing templates configured for the activity being performed by the individual and a look-up table having entries for the plurality of pacing templates; a clock; an activity completion module; an output device; a processor in communication with the PSS module, the memory, the clock, the activity completion module, and the output device, the processor configured to receive a strain signal from the PSS monitor, receive a time from the clock, receive a signal from the activity completion module representing an amount of the activity completed by the individual, calculate a physiological strain index (PSI) from the strain signal, selecting one pacing template based on the PSI, the time, the amount of the activity completed using the look-up table in the memory, and outputting information in the pacing template to the output device.

Further to any of the above embodiments, the system further including a housing that holds 1) the memory, the clock, the output device and the processor; 2) the memory, the clock, and the processor, or 3) the heart rate monitor or the PSS module, the memory, the clock, the output device and the processor. Further to any of the above embodiments, where the heart rate monitor communicates with the processor wirelessly. Further to any of the above embodiments, where at least one of 1) the heart rate monitor or the PSS module and 2) the output device communicates with the processor wirelessly. Further to any of the above embodiments, the output device includes at least one of a display, a speaker, and a transducer.

Further to any of the above embodiments, the activity completion module is selected from a group consisting of a pedometer, an accelerometer tracking distance travel, a bicycle computer tracking cycling distance, and an odometer tracking cycling distance; or the activity completion module includes at least one of a pedometer, an accelerometer tracking distance travel, a bicycle computer tracking cycling distance, an odometer tracking cycling distance, or a Global Positioning System. Further to any of the above embodiments, the processor selects a pacing template at predetermined time intervals or predetermined intervals based on percentage of activity completed.

Further to any of the above embodiments, the system further including at least one atmospheric sensor in communication with the processor; and the processor uses a signal received from the at least one atmospheric sensor in selecting a pacing template. Further to the previous embodiment, the atmospheric sensor includes a temperature sensor and/or a humidity sensor.

Further to any of the above embodiments, the system further includes an internal temperature sensor adapted to be in the individual and in wireless communication with the processor to provide a body core temperature for the individual, where the body core temperature and the heart rate are used to determine the PSI. Further to any of the above embodiments, the system further includes a clothing module configured to receive input regarding the clothing being worn by the individual. Further to any of the above embodiments, the system further includes an input for receiving identification of the activity being performed by the individual.

In at least one embodiment, a method for recommending by a processor a pace to an individual based on an activity and physiological state of the individual, the method including at predetermined intervals receiving a heart rate for the individual from a heart rate monitor attached to the individual; receiving a time signal from a clock; receiving a representation of an amount of the activity completed by the individual; determining a physiological strain index (PSI) based on the received heart rate; using the PSI, the received time signal, the representation of the amount of the activity completed to select a pacing template from a plurality of pacing templates contained in storage; providing pacing information based on the selected pacing template to the individual.

In at least one embodiment, a method for recommending by a processor a pace to an individual based on an activity and physiological state of the individual, the method including at predetermined intervals receiving a heart rate for the individual from a heart rate monitor attached to the individual; receiving a representation of an amount of the activity completed by the individual; determining a physiological strain index (PSI) based on the received heart rate; using the PSI and the representation of the amount of the activity completed to select a pacing template from a plurality of pacing templates contained in storage; providing pacing information based on the selected pacing template to the individual.

Further to the previous method embodiments, the method further receiving a body core temperature from a temperature sensor internal to the individual; and where the PSI is determined based on the body core temperature and the received heart rate.

A method for recommending by a processor a pace to an individual based on an activity and physiological state of the individual, the method including at predetermined intervals receiving a strain signal for the individual from a physiological strain state (PSS) module; receiving a representation of amount of the activity completed by the individual; determining a physiological strain index (PSI) based on the received strain signal; using the PSI and the representation of the amount of the activity completed to select a pacing template from a plurality of pacing templates contained in storage; providing pacing information based on the selected pacing template to the individual. Further to the previous embodiment, the PSS being determined at least in part based on the body core temperature obtained from a sensor or predicted based on heart rate.

Further to the previous method embodiments, the method further including receiving at least one atmospheric condition from an atmospheric sensor; and using the at least one atmospheric condition to select a subset of pacing templates from which the processor selects a pacing template based on the PSI, the received time signal and the representation of the amount of the activity completed. Further to the previous method embodiments, where the activity is selected from a group consisting of a run, a bicycle ride, a hike, a swim, a climb, a walk, a cardiovascular workout, cleaning, washing a vehicle, skating, and any combination of these activities. Further to the previous method embodiments, the method further including transmitting the pace information and physiological information to an external device collecting information from a plurality of individuals. Further to the previous method embodiments, the method further including receiving at least one of clothing being worn by the individual and the activity being performed by the individual.

Further to any of the previous embodiments, the pacing guidance or recommended pace is for a particular action or a series of discrete actions. Further to the embodiments having a heart rate monitor, the heart rate monitor is replaced by a physiological strain state module configured to provide a PSI based on physiological data and/or a self-reported RPE/thermal sensation scale score received from the individual.

Further to any of the previous embodiments, the PSI is replaced by an adaptive PSI.

IV. BRIEF DESCRIPTION OF THE DRAWINGS

FIGS. 4A-4I illustrate learned discrete transition probability distributions where current PSI state is indicated by a vertical line. The learned discrete probability distribution is shown as a grey scale heat map, white shows the highest density, black=0. Overlaid are the offset learned linear regression equations.

Figures 5A, 5B:
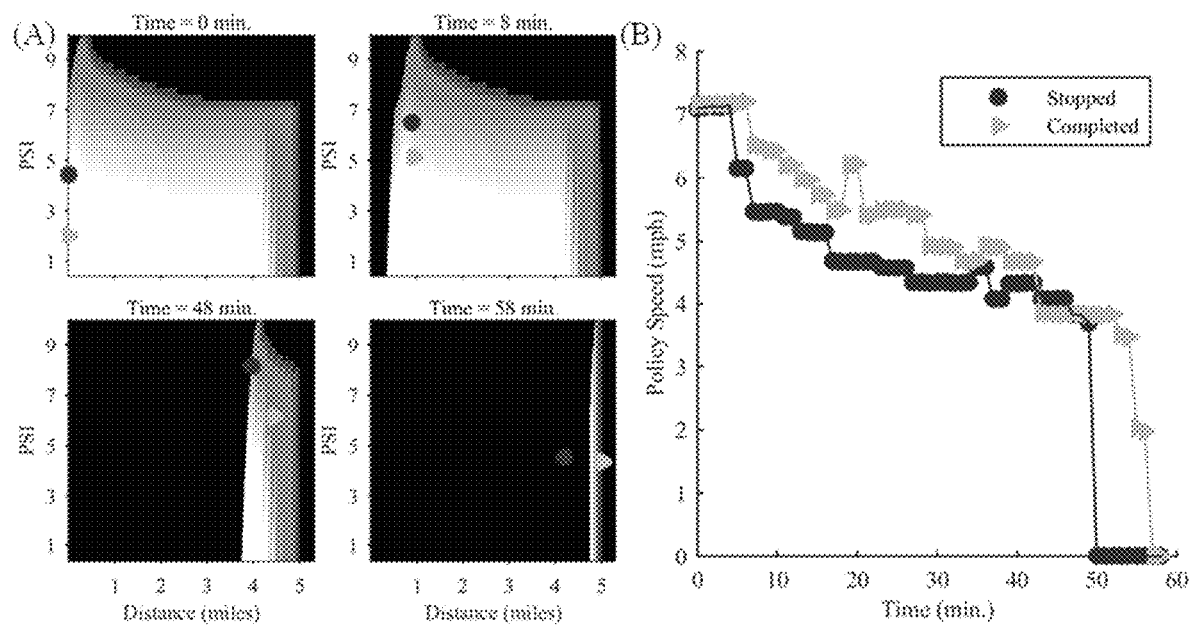
Figure 4A:
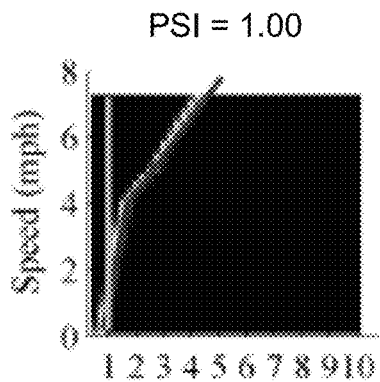
Figure 4B:
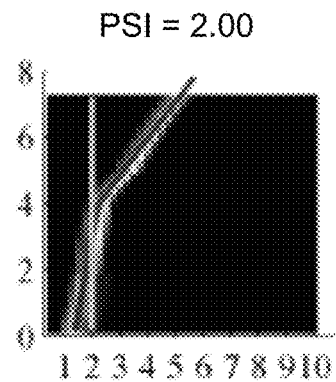
Figure 4C:
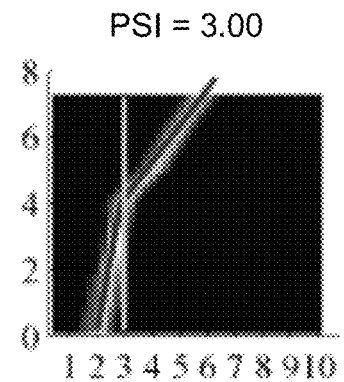
Figure 4D:
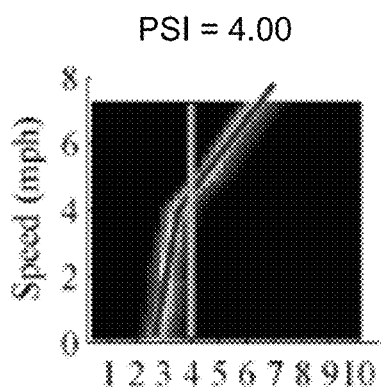
Figure 4E:
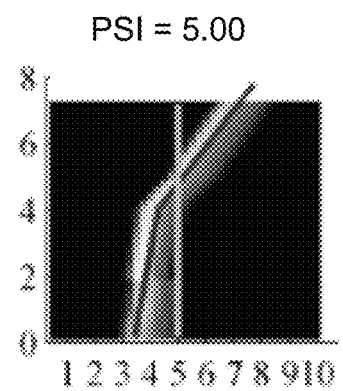
Figure 4F:
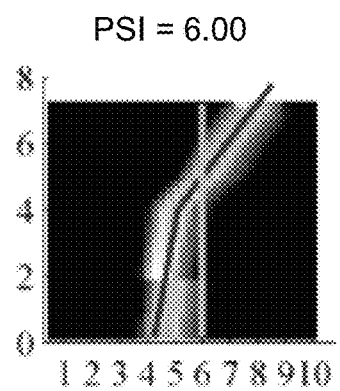
Figure 4G:
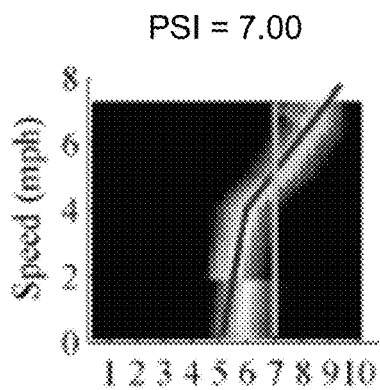
Figure 4H:
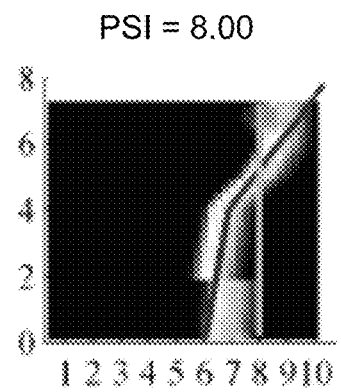
Figure 4I:
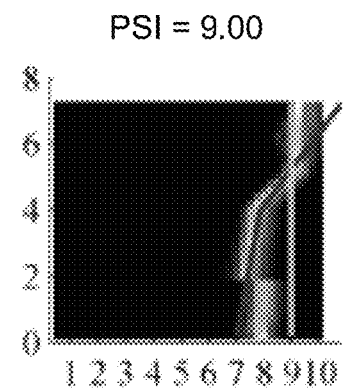

FIG. 5A illustrates a computed pacing template for minutes 0 (start pace), 8, 48, and 58 (end 2 min. pace). Pace is selected based upon the time into the exercise, the distance completed (x-axis), and the subjects' current physiological strain index (PSI) (y-axis). Lighter colors indicate fast movement speeds (white=7 mph and black=0 mph). Distance and PSI are shown for two subjects, one guided to stop (circle), and one to complete the five miles (triangle). FIG. 5B illustrates a template selected pace for the subject who was stopped and the subject who completed the task for each two minute period during the GUIDED session.

Figure 6A:
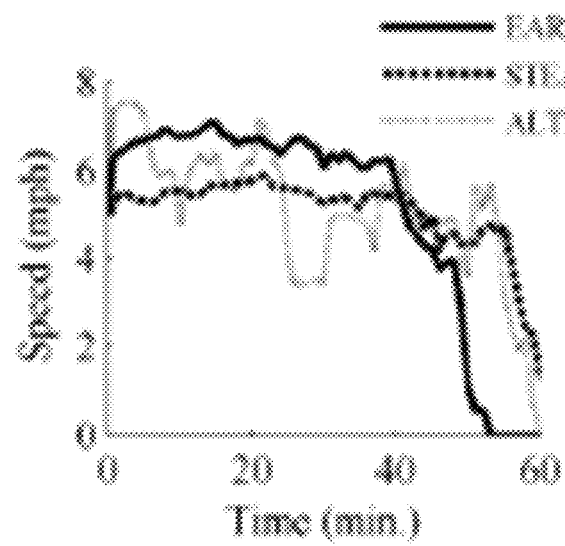
Figure 6B:
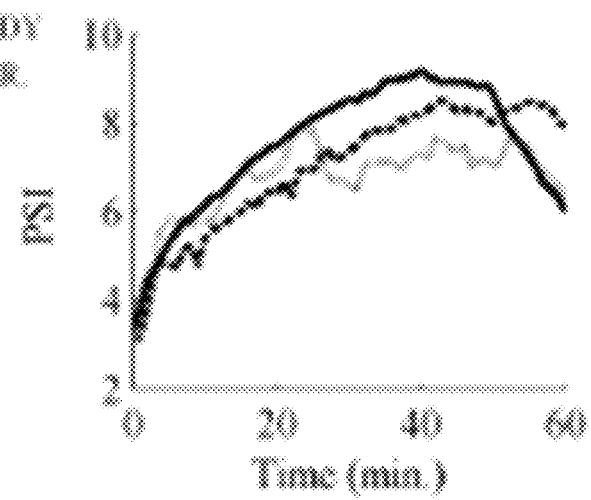

FIG. 6A illustrate Mean speed for each of the three movement groups. FIG. 6B illustrate Mean PSI for each of the three movement groups.

Figure 7A:
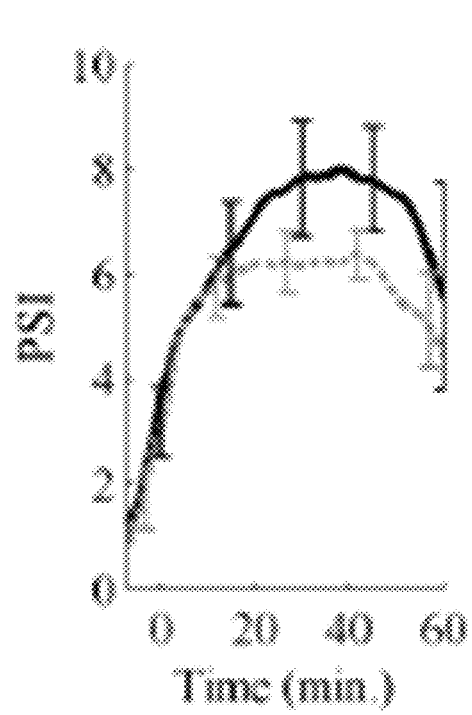
Figure 7B:
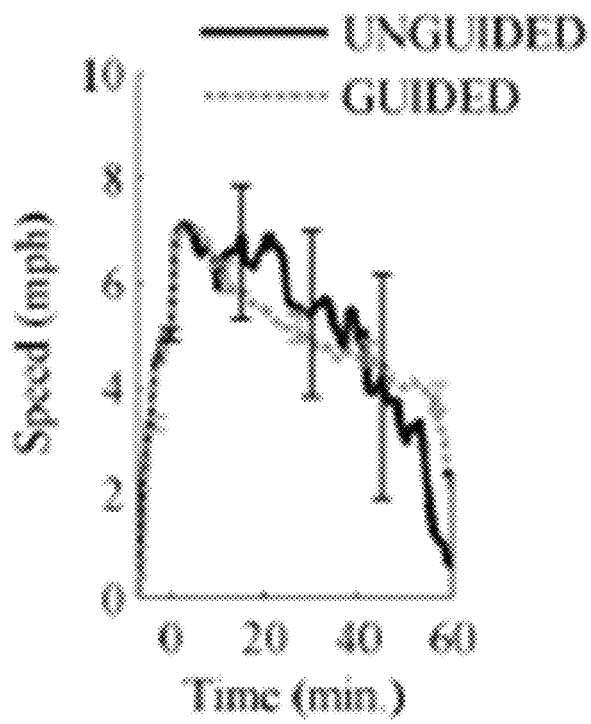

FIG. 7A illustrate Mean PSI for volunteers completing both the GUIDED and UNGUIDED exercise sessions. FIG. 7B illustrate Mean speed for volunteers completing both the GUIDED and UNGUIDED exercise sessions.

Figure 8:
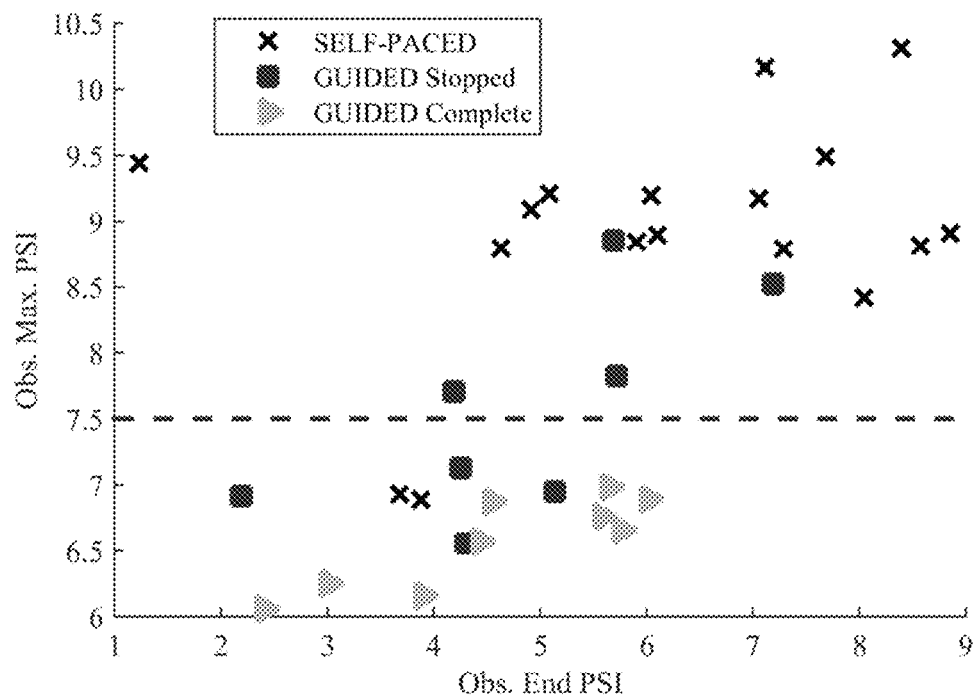
Figures 9A, 9B, 9C:
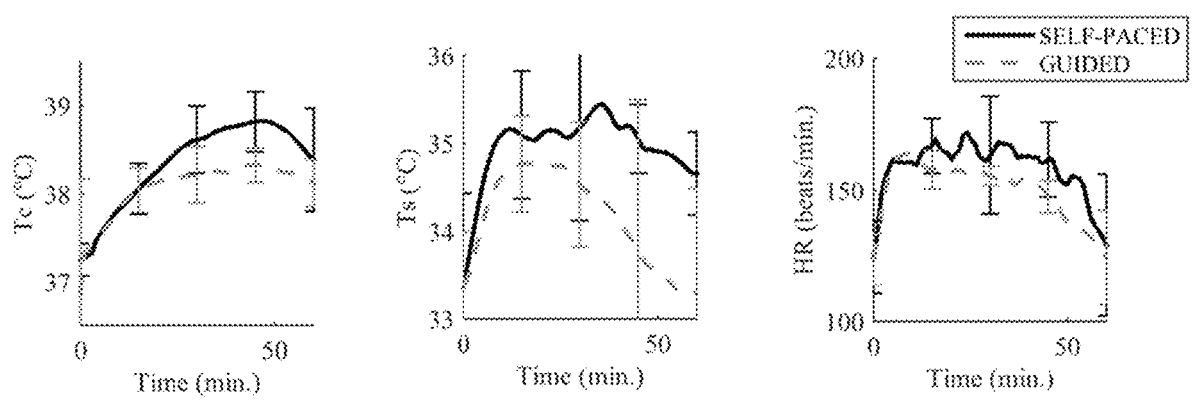
Figure 9D:
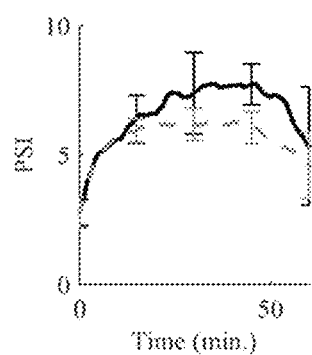
Figure 9E:
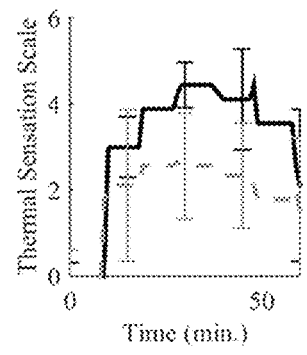
Figure 9F:
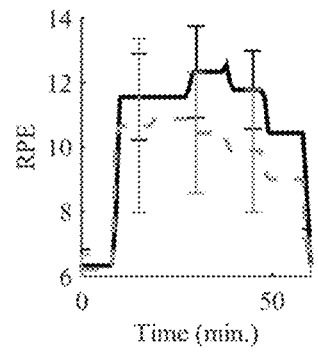

FIG. 8 illustrates an end-point by maximum observed PSI for all subjects for both the GUIDED (squares and triangles) and SELF-PACED (or UNGUIDED) (X) sessions indicating those guided to completion (triangle) and those guided to stop (circle). A dashed red line indicates the 7.5 PSI threshold used to provide penalties in the MDP definition.

FIGS. 9A-9F illustrates Mean Tc, Ts, HR, PSI, Thermal Scale, and RPE for both GUIDED (dashed lines) and SELF-PACED (solid lines) sessions. The error bars are ±1 standard deviation.

Figure 10:
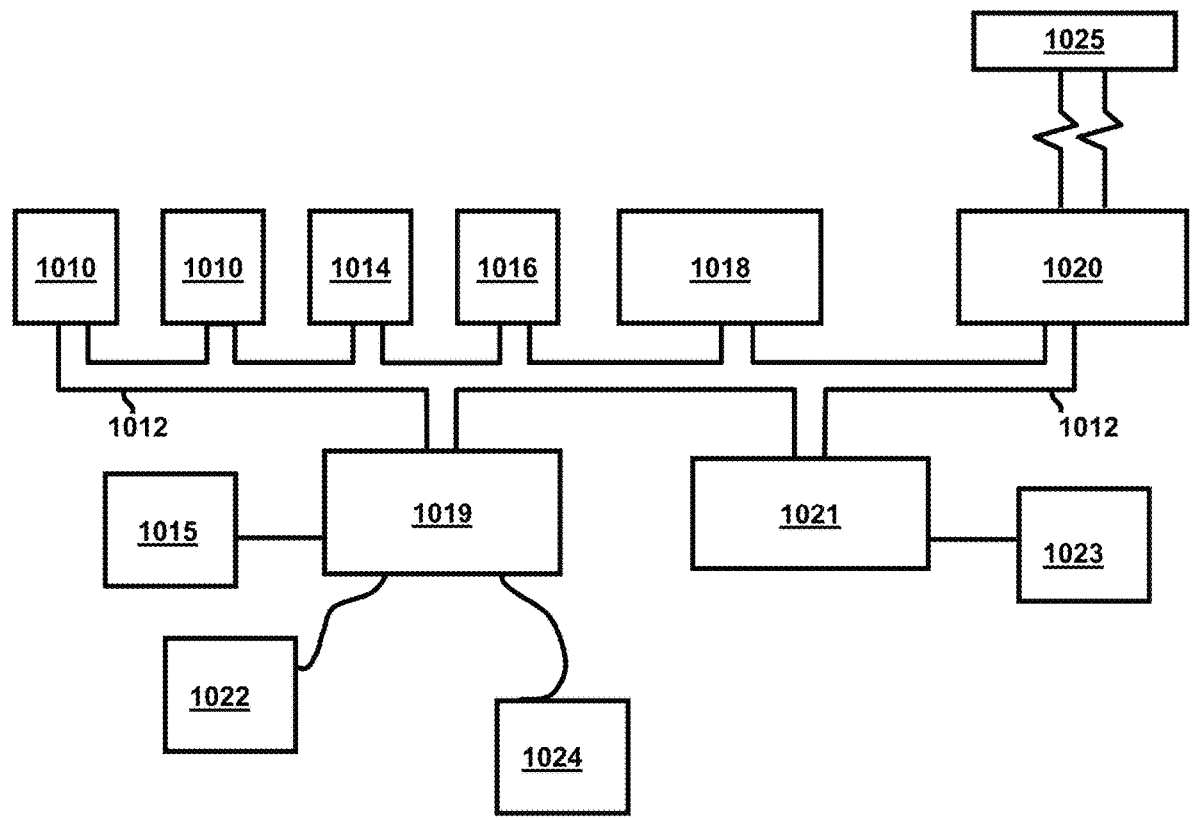

FIG. 10 illustrates a computer program product and computer implementation according to at least one embodiment of the invention.

V. DETAILED DESCRIPTION OF THE DRAWINGS

In at least one embodiment, a system and/or a method estimate a thermal-work strain health state based on at least a series of sequential measurements of heart rate, which in at least one embodiment is the sole basis, and selects a pace based upon the individual's current thermal work strain state, which is an example of physiological strain state (PSS), overall task goal and in many implementations thermal safety constraints. In a further embodiment, the system and/or the method estimate the PSS based on the heart rate measurements and at least one of body core temperature and skin temperature. In at least one embodiment, the pacing templates are developed using a thermoregulatory model that is used in Monte Carlo simulations where the definition of state space, rewards, and penalties are based on upon the activity that the individual will be doing.

In at least one embodiment, the actions may be a series of movements at different speeds interspersed with rest periods to accomplish the goal. These movement speeds will have different impacts on the thermal-work strain state of the individual, and progress to the ultimate goal. By perceiving the thermal-work strain state, our problem is to optimally control the pace of the individual to minimize immediate heat illness/stroke risk and to allow completion of the goal with the least thermal-work strain possible.

Figure 1A:
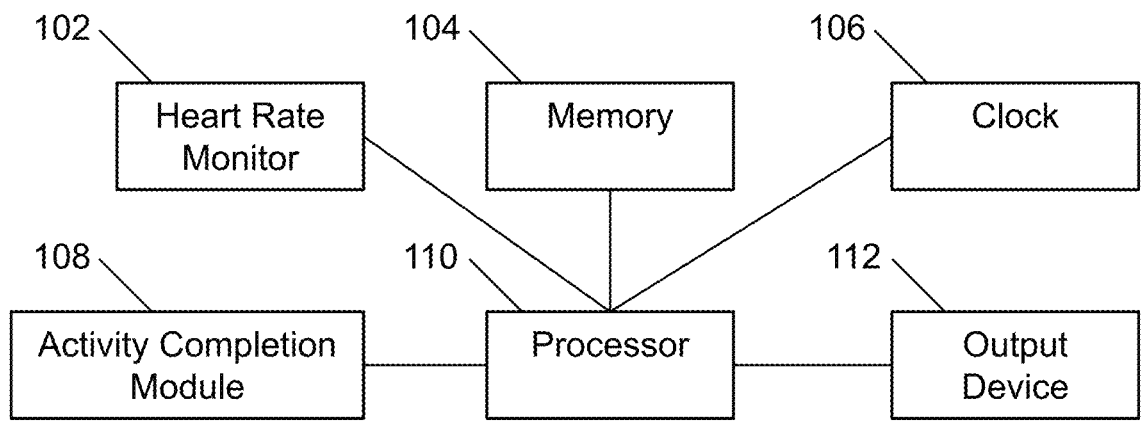
FIGS. 1A-1F illustrate systems according to different embodiments of the invention.

FIG. 1A illustrates a system according to at least one embodiment that includes a heart rate monitor 102, a memory 104 containing a plurality of pacing templates organized in a look-up table, a clock (or timing system) 106, an activity completion module 108, a processor 110, and an output device 112 such as a display, a speaker, a transducer adapted to vibrate against the individual's skin and/or other mechanism capable of providing pacing information. The processor 110 is in communication with the heart rate monitor 102, the memory 104, the clock 106, the activity completion module 108, and the output device 112. The communication between the components may be direct or indirect and wired or wirelessly depending upon a particular implementation.

The processor 110 uses information from a heart rate signal outputted by the heart rate monitor 102 to determine an estimated body core temperature of a person (or individual) using the system. In at least one embodiment, the body core temperature and the heart rate are used to determine a Physiological Strain Index (PSI). The processor 110 uses information from the activity completion module 108 to determine how far along the activity has been completed and/or how much remains, and in a further embodiment based on activity completion information entered into the system via for example, an interface usable by the individual or wirelessly from an external device. The processor 110 uses at least one of the body core temperature and the PSI in addition to the level of activity completion and/or time elapsed to look-up a pacing template in the memory 104 to provide an updated pace for performing the activity to the individual. The pacing information is provided by the processor 110 to the output device 112. Alternatively, the output device is omitted and the information is provided to an external device that provides the information to the individual, another party, or an external device. In an alternative embodiment, the clock 106 may be omitted when there is not a time requirement or time-based goal.

Examples of the heart rate monitor 102 includes a heart rate sensor attached to the subject person, a processor for receiving EKG signals from electrodes attached to the person, a processor for receiving a photolthysmogram signal (e.g., a pulse oximeter), or a processor for receiving a ballistic-cardiogram signal.

The memory 104 may take a variety of forms known in the art to store the pacing templates and in at least one embodiment a look-up table that includes at least one entry for each pacing template. The look-up table is used by the processor 110 in such an embodiment to select the applicable pacing template. In at least one embodiment, the memory also stores any physiological data collected by the processor and pacing recommendations for later use such as analysis and/or aggregation from additional similar devices. In at least one embodiment, the memory 104 also stores heart rate and temperature data from the processor 110.

Examples of an activity completion module 108 include, but are not limited to, a pedometer and/or accelerometer tracking distance travel, a bicycle computer or odometer tracking cycling distance, a Global Positioning System (GPS). In a further embodiment, the activity completion module 108 is a series of devices for different stages of the activity being performed by the individual based on their current activity stage. Examples of this particular implementation include a triathlon and an activity made up of a series of discrete actions. In a further embodiment, the activity completion module 108 receives user input when the next stage starts or based upon detected conditions (e.g., a decrease in pressure from leaving the water), the activity completion module 108 determines a change in actions/activity. In at least one embodiment, the activity completion module also utilizes the processor 110 or another suitably programmed processor to track the amount of the activity completed with respect to the overall activity being performed by the individual.

In at least one embodiment, the processor 110 determines an updated pacing information on a predetermined update schedule (or intervals) based on time intervals, level of activity completion (or activity completed), and/or time elapsed. Examples of time include 30 seconds, one minute, two minutes, five minutes, ten minutes, any time between 15 seconds and 60 minutes including the end points, and any time between one minute and 30 minutes including the end points. Examples of activity completed are percentages of the activity completed such as 1%, 5%, 8%, 10%, 15%, fall within a range of 1% and 25% including the end points, and fall within a range of 1% and 20% including the end points. Similar percentages may be used for time elapsed versus an expected length of time for the activity. Additional predetermined intervals include using any measurement units that are associated with the activity such as distance for walking, running, cycling, and swimming; elevation height traveled for climbing; and the number of tasks performed that make up the activity. In a further embodiment, updated pacing information is monitored substantially continuously. In another embodiment, the pacing information is updated on demand. Furthermore, in at least one embodiment, these different updating approaches are used in a variety of combinations with each other.

Figure 1B:
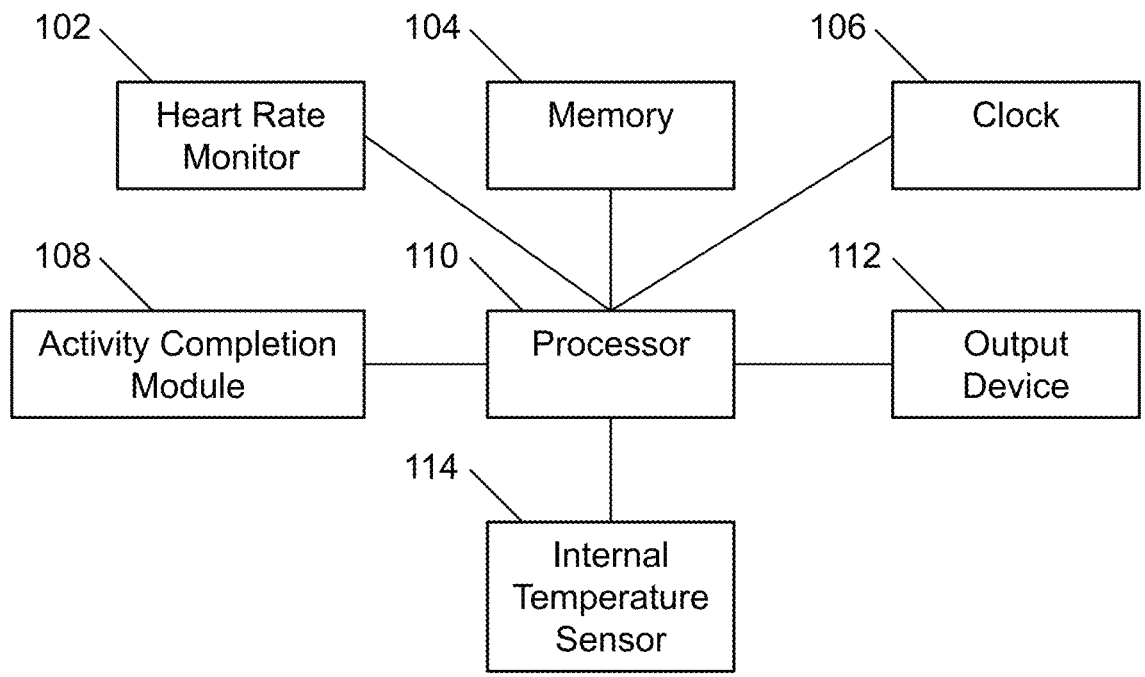

In an alternative embodiment, the system further includes an internal temperature sensor 114 illustrated in FIG. 1B instead of having the processor 110 estimate a body core temperature. Examples of the internal temperature sensor 114 include a thermometer pill (e.g., MiniMitter Jonah thermometer pill) orally ingested by the individual or an implanted sensor in the individual. The temperature sensor 114 in at least one embodiment would be in wireless communication with the processor 110.

Figure 1C:
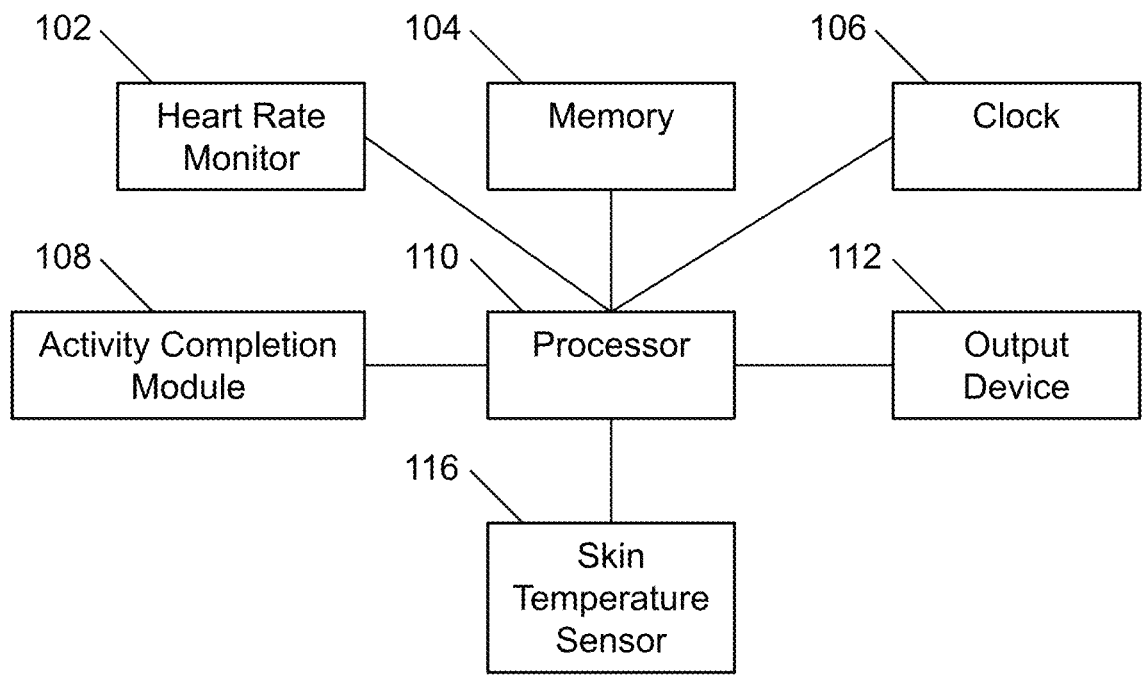

In a further embodiment to the above embodiments, the system illustrated in FIG. 1C further includes a skin temperature sensor 116 that is attached to the individual being monitored to provide a signal representing skin temperature for the individual. In at least one embodiment, the skin temperature can provide a temperature gradient with the body core temperature that may, for example, be used in calculating PSI as discussed below.

Figure 1D:
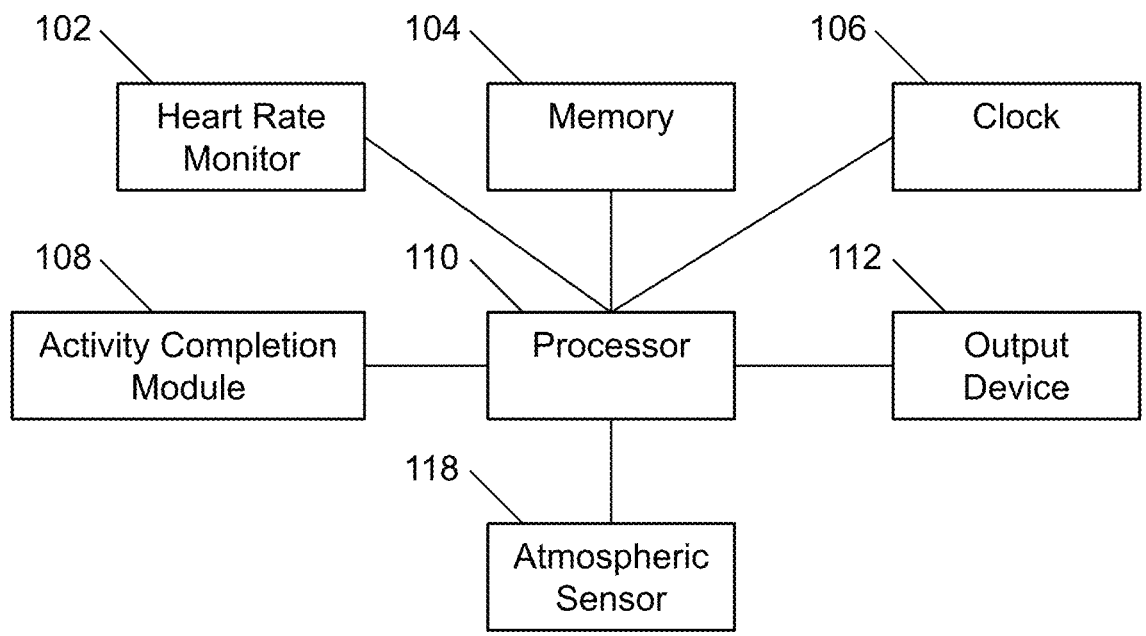

FIG. 1D illustrates a further embodiment to the above embodiments that adds at least one atmospheric sensor 118. In at least one embodiment, the atmospheric sensor provides a signal representative of at least one current environmental characteristics such as temperature, humidity, wind, light level, barometric pressure, and particles present in the atmosphere (e.g., pollen or ash). The environmental information may be used by the processor 110 to select a sub-set of pacing templates based on the environmental information. In an alternative embodiment, the environmental characteristics are obtained from a weather service or other external source such as wirelessly over a network such as a telecommunications network including cellular (e.g., 3G, 4G, LTE, etc.), a WiFi network, and a local area network.

Figure 1E:
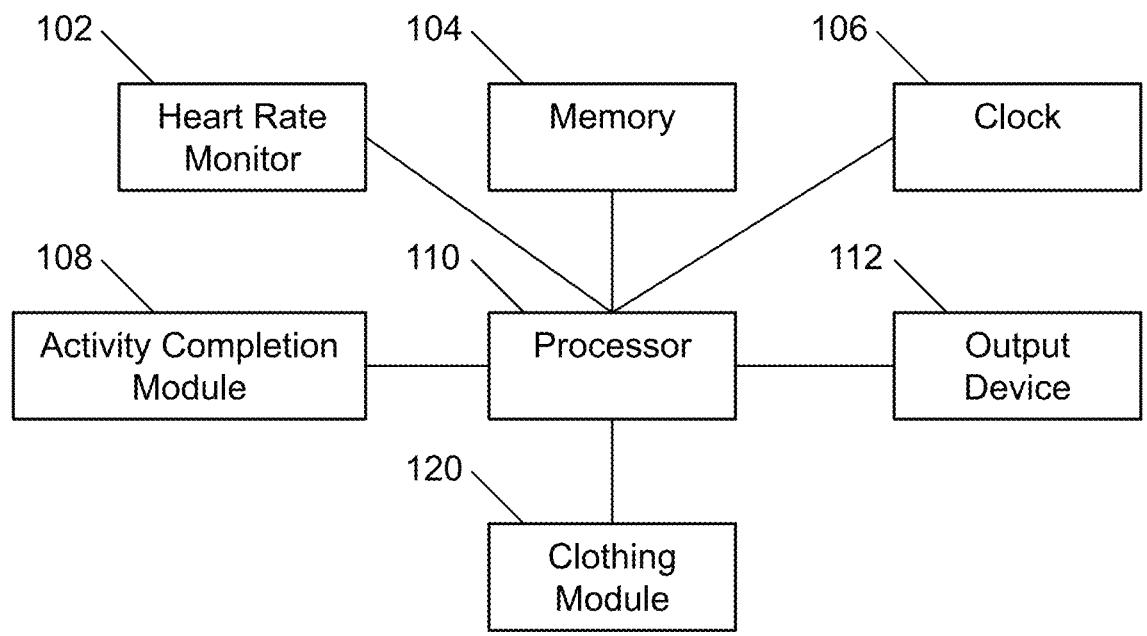

FIG. 1E illustrates a further embodiment to the above embodiments that adds a clothing module 120. The clothing module 120 allows for entry into or selection from a list of clothing that is being worn by the individual being monitored during the activity. The entry may be done by the individual or another person or even an external sensor or system that is in communication with the clothing module 120. An example is that a firefighter will wear protective gear that impacts the firefighter's ability to dissipate heat as compared to a long distance runner wearing shorts and a shirt. In at least one embodiment, the type of clothing being worn impacts the relevant pacing templates to be used. In this embodiment, the pacing templates also include sub-sets of pacing templates based on clothing from which the relevant pacing template is selected for the activity. In a further embodiment being worn by the individual, the clothing being worn will impact the thermal safety constraints used, for example by reducing them if there is reduced heat dissipation being possible based on the clothing. In at least one embodiment, the input used for the clothing module 120 may also be used separately or independent of clothing selection to select or enter the activity or activities being performed by the individual and in further embodiments the parameters under which the pacing templates are selected in an implementation where the storage includes pacing templates for different activities.

Figure 1F:
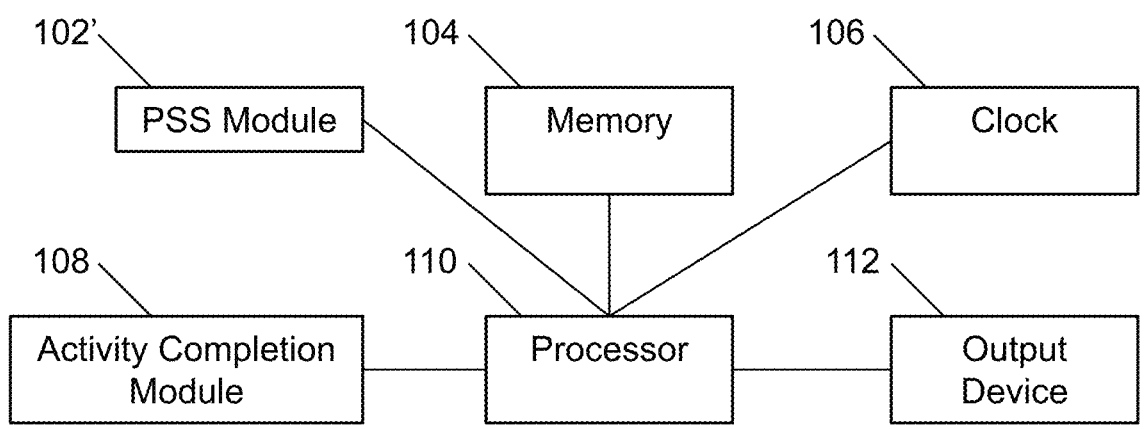

FIG. 1F illustrates a system embodiment having a physiological strain state (PSS) module 102' in place of the heart rate monitor 102 of FIG. 1A. The PSS module 102 in at least one embodiment includes a heart rate monitor 102 or other component that will facilitate determining a PSI based on physiological data. In an alternative embodiment, the PSS module 102' includes an interface that allows for the individual to self-report rating of perceived exertion (RPE) and/or thermal sensation scale score during performance of the activity being paced. The self-reported information then is used by the PSS module 102' to provide an input to the processor 110, which then can make the pacing recommendation using the PSS module 102' input. In at least one embodiment, the PSS module 102' is code running on the processor 102 to provide a user interface to facilitate interaction with the user regarding the self-reported information and then to provide this to the processor 110. An example of the interface includes a graphical interface on a display, one or more buttons (physical or virtual) to facilitate the user to make a selection or entry of the self-reported information when prompted by the system or as the individual feels there is a change (for example, hitting a button to increase or decrease the level of exertion felt, cramping, approaching bonk (i.e., hit the wall) in an endurance sport, bonking in an endurance sport).

Based on this disclosure, it should be appreciated that the different components discussed in connection with FIGS. 1B-1E including the skin temperature sensor 116, the atmospheric sensor 118, and the clothing module 120 may be combined with each other in different combinations. Based on this disclosure, it should be understood that the PSS module 102' from FIG. 1F may be substituted for the heart rate monitor 102 in FIGS. 1B-1E and be used in various combinations with the skin temperature sensor 116, the atmospheric sensor 118, and the clothing module 120.

In at least one embodiment, the system further includes a housing in which the various components are placed. In a further embodiment, the housing may include antennas to facilitate wireless communication by the processor 110 through for example a transmitter, a receiver, etc. In at least one embodiment, the processor 110, the memory 104, and the clock 106 are located in the housing with the output device present in it or on it. In further embodiments, the heart rate monitor 102 and/or the activity completion module 108 are also present in or on the housing. In at least one embodiment, the housing may also provide sufficient spacing from the wearer of the system to place the at least one atmospheric sensor 118 in those embodiments with that sensor. The housing may, for example, be wrist worn, ankle worn, arm worn, included within a smartphone or other electronic device, mounted on a belt or strap worn by the individual, mounted on equipment worn by the individual. In a further embodiment, the system is incorporated into a watch.

In at least one embodiment, the body core temperature is calculated in a multi-step process using an extended Kalman filter as discussed in U.S. Pat. App. Pub. No. US-2014-

0180027-A1 based on heart rate values, which is hereby incorporated by reference. In other embodiments, the body core temperature is calculated using a Kalman filter as discussed in Buller et al., "Estimation of Human Internal Temperature from Wearable Physiological Sensors," IAAI, 2010, which is hereby incorporated by reference. In at least one embodiment, using any known way to estimate a body core temperature including using any combination of skin temperature, physiological data, accelerometer data, environmental information, and clothing information.

A PSS can be represented in a number of ways including a simple index to relate the physiological measures. There are a variety of ways to calculate such a physiological strain index (PSI) based on the body core temperatures and heart rates at the start (or rest) and current values. One example is using the approach taught by Moran et al. for calculating PSI. Moran D S, Shitzer A, Pandolf K B, "A physiological strain index to evaluate heat stress," Am. J. Physiol. 1998; 275(1 Pt 2):R129-134.

$$PSI = 5\left(\frac{CT_t - CT_{rest}}{39.5 - CT_{rest}}\right) + 5\left(\frac{HR_t - HR_{rest}}{180 - HR_{rest}}\right)$$

In at least one embodiment, the following equation is used for determining an adaptive PSI (aPSI) score in at least one embodiment is as follows:

$$aPSI = 5\left(\frac{CT_t - CT_{rest}}{CT_{critical} - CT_{rest}}\right) + 5\left(\frac{HR_t - HR_{rest}}{HR_{critical} - HR_{rest}}\right)$$

$$HR_{critical} = 0.90(220 - age)$$

$$CT_{critical} = 39.5 + \frac{(CT - ST) - 4}{4}$$

In the adaptive PSI equation, the CTt is the body core temperature at a time t, $CT_{rest}$ is the body core temperature at rest, $HR_t$ is heart rate at a time t, and the $HR_{rest}$ is heart rate at rest, the $HR_{critical}$ is the heart rate at a critical rate. In at least one embodiment The $HR_{critical}$ in the adaptive PSI equation has a value as 90% of $HR_{max}$ as suggested by the American College of Sports Medicine Guidelines (America College 1991) and also includes the variable (220-age) for the $HR_{critical}$ value to be configured to apply to individuals of any age. In an alternative embodiment, the $HR_{critical}$ can be set as 90% of $HR_{max}$ derived from a VO2 max test. In at least one embodiment, the $HR_{critical}$ is determined for the particular person based on previous physiological measurements.

The adaptive PSI equation also includes $CT_{critical}$ as the critical body core temperature and can be based on calculating a standard core temperature (CT), a skin temperature gradient (ST), and a critical temperature such as 39.5° C. During activity the $CT_{critical}$ will vary based on a temperature gradient between the current core temperature and the current skin temperature.

The adaptive PSI equation in at least one embodiment adjusts the detection of a heart rate for comparison to a standard average heart rate for a person, such as 180 beats/minute. For example, the $HR_{critical}$, such as a critical temperature for an individual fully encapsulated in personal protective equipment (e.g. hazmat suit), can be an uncompensable heat strain and make the individual less able to tolerate high body core temperatures. In at least one method embodiment, the adaptive PSI equation modifies the physiological strain index for a clothing garment that encloses the wearer and can create an index that uses an individual physiology to adapt the heat strain index score.

The pacing templates can be thought of as "control policies" that are used to optimize some aspect of a dynamical system. A pacing dynamical system would be composed of physiological and task-completion states, a set of pacing actions, and physiological rules that govern how the states change over time. The control problem is to pick a pace such that performance is optimized with regards to homeostatic constraints. When these dynamical systems are represented in a discrete stochastic form, such as a Markov Decision Process (MDP) (Bellman, R E, "A Markov decision process," Journal of Mathematical Mechanics, 1957, vol. 6, pp. 679-684), optimal control policies can be computed a priori.

Figure 2:
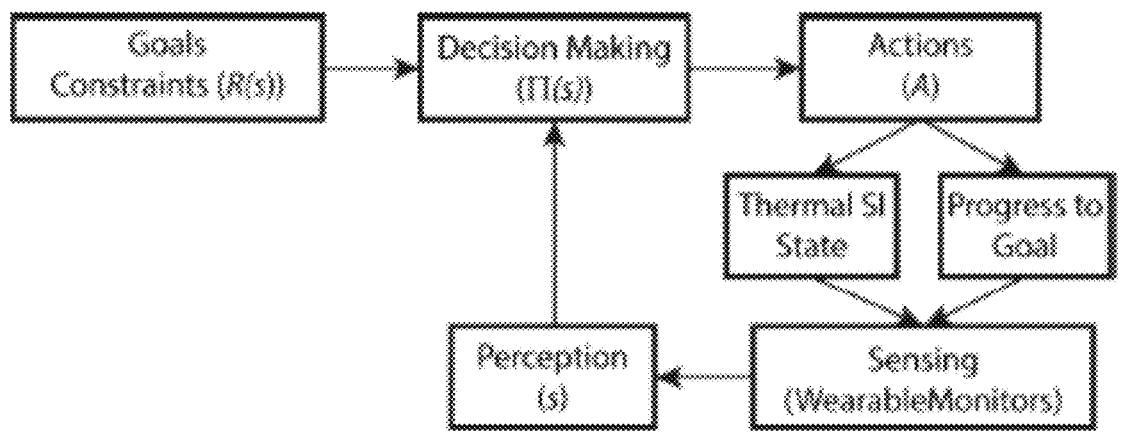
FIG. 2 illustrates the Physiological Feedback Loop where s=state (human PSS indicated by the physiological strain index (PSI), distance to goal and time), R is a reward function dependent on state. Π=a policy function dependent upon state, and A=actions (movement speed or pace).

In at least one embodiment, the processor 110 provides the automated pacing guidance based upon a physiological feedback loop. FIG. 2 illustrates an example of a physiological feedback loop. In FIG. 2, s=state (PSS indicated by the PSI index, distance to goal and time), R is a reward function dependent on state. Π=a policy function dependent upon state, and A=actions (movement speed or pace) developed based on a dynamical system. Examples of the sensing wearable monitors include the heart rate monitor 102 and the activity completion module 106.

In at least one embodiment, the perception of the thermal-work strain state is PSI estimated from measurements of heart rate and estimates of $T_{core}$ using sequential measures of heart rate. As mentioned previously, the core temperature estimation algorithm may be based on an extended Kalman filter, which is comprised of two relationships: a time update model and an observation model. In the estimation of $T_{core}$ the time update model relates how $T_{core}$ changes from time-step to time-step along with the uncertainty/noise associated with this change. The observation model relates an observation of heart rate to a $T_{core}$ value along with the uncertainty of this mapping. The models were developed based on field data from young (23±4 yrs) Soldiers with a large range of body core temperature values (36° C. to 40° C.).

The thermal-work strain state was used to select a movement speed (action (a)) from a policy estimated from a MDP, that balanced goals of the movement task, and the thermal-work strain safety constraints. The MDP will be discussed in terms of the experiment discussed later in this disclosure relating to covering a distance of 5 miles within 1 hour while attempting to minimize PSI.

A MDP is defined by a set of states (S), a set of actions (A), a state transition probability mass function (PMF) and a reward function R(S). For this laboratory study the set of states and actions were well defined. The state transition PMF was estimated from a physics/physiology based human thermoregulatory model.

State definition is used to specify the state of the task. In the experiment discussed in connection with the experiment discussion later there were three states: 1) time completed (t), 2) the thermal-work strain of the subject (PSI), and 3) distance completed (D). Time completed was discretized into two minute increments where t:={0, 2, . . . , 58, 60} although as mentioned previously different increments may be used depending on the desired frequency and/or resolution of data analysis with updated recommendations. Thermal-work strain state was discretized into 0.25 PSI units starting at 0.5 and ending at 10 where PSI:={0.5, 0.75, . . . , 9.75, 10}. Distance (D) completed was discretized into units of 0.0067 miles or the fraction of a mile that can be completed at 0.2 miles per hour (mph) within 2 minutes where D:={0, 0.0067, . . . , 5.9933, 6} although other distances or measurements of completion may be used.

Action definition relates to the type of possible actions that may occur. In an example involving covering a certain amount of distance, actions were constrained to movement speeds from 0 to 7 mph in 0.2 mph increments. Except for no movement (0 mph) speeds less than 2 mph were excluded as they are not typical movement speeds and would be more awkward than helpful to a pacing strategy. Thus A:={0, 2.0, 2.2, . . . , 6.8, 7.0}. These actions were the same for every state.

Figure 3A:
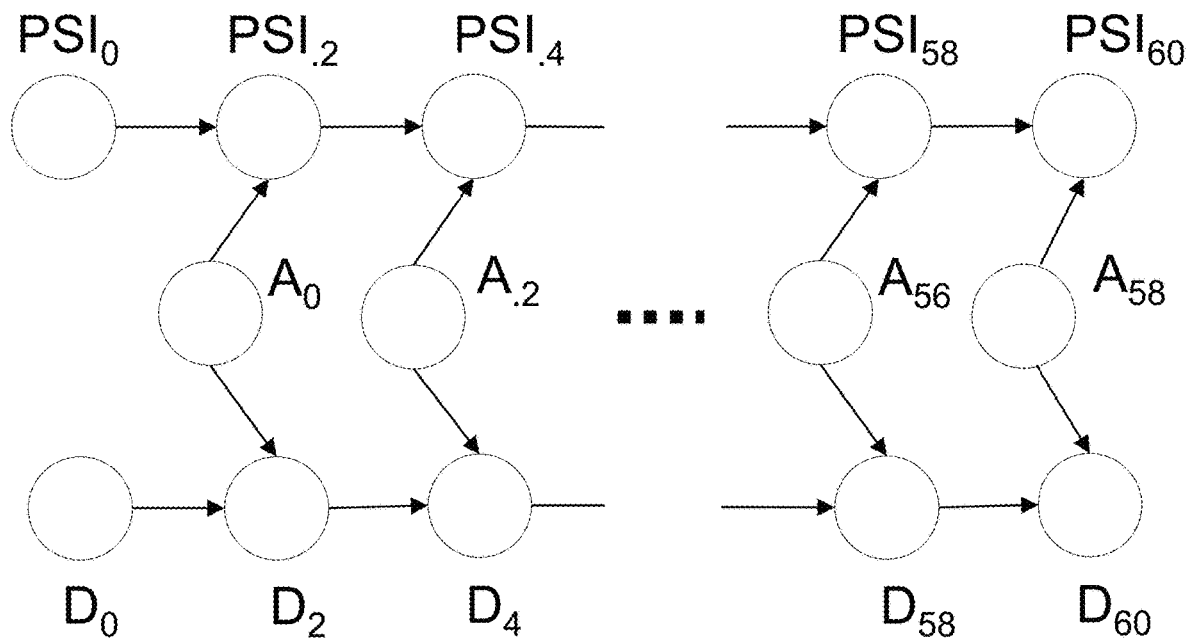
FIG. 3A illustrates a graph representation of the State-Action Space where PSI is the thermal work strain index, which is an example of PSS, D is distance, and A is action.
Figure 3B:
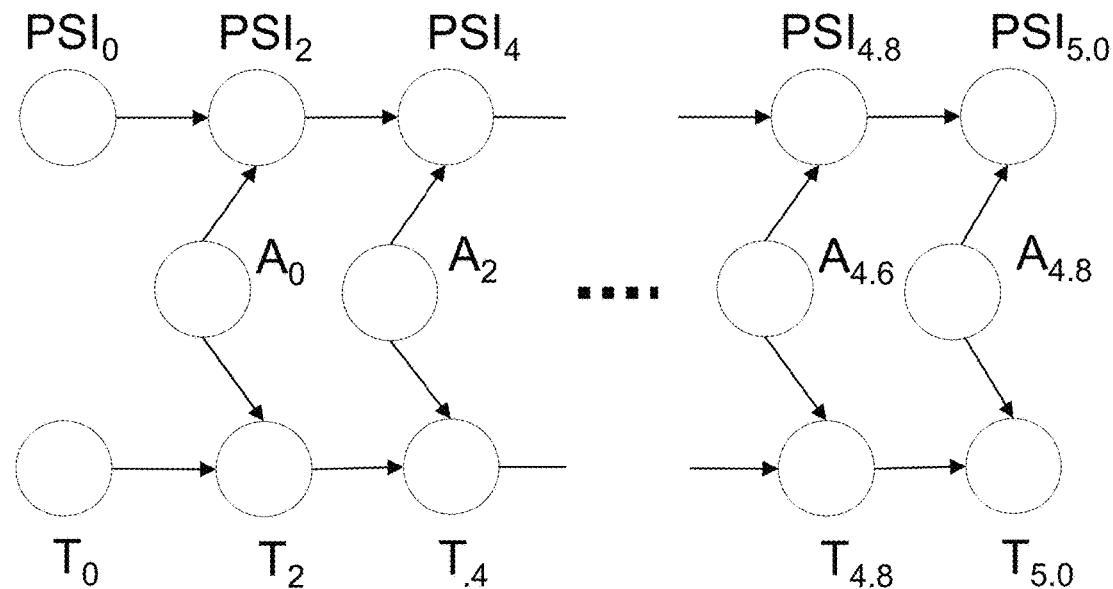
FIG. 3B illustrates a graph representation of the State-Action Space where PSI is the PSS, T is time, and A is action.

In the experiment discussed in this disclosure, the final state action space was comprised of 30×39×900 (t×PSI×D) discrete states with 27 actions permissible from each of these states. FIG. 3A illustrates the resulting directed acyclic graph that represents the state-action space where PSI is the physiological strain state, D is distance, and A is action at different times. In an alternative embodiment, the state action space could replace distance at particular times with times at particular distances where the distance also serves as the subscript for PSI and actions A. FIG. 3B illustrates a state action space for the five mile distance of the experiment taken at 0.2 mile increments.

In the experiment, the MDP had two transition PMFs. The transition PMF gives the likelihood of transitioning to each state (i.e., next PSI state and next distance-from-goal state after 2 minutes of time) given a subject's current state when they take an action (e.g., walk or run at some speed). A physics/physiology based thermoregulatory model (Kraning K K, Gonzalez R R, "A mechanistic computer simulation of human work in heat that accounts for physical and physiological effects of clothing, aerobic fitness, and progressive dehydration," *Journal of Thermal Biology*, 1997; vol. 22(4/5): pp. 331-342) (SCENARIO Model at http://www.usariem.army.mil/index.cfm/modeling/scenario) was used to learn the transition probabilities by Monte Carlo approximation. For any action undertaken there will be a certain amount of distance completed and a change in the PSI state. For the distance transition probability mass function we placed a small amount of uncertainty (N(0,0.2)) around the distance travelled in 2 minutes. The transition probability mass function is shown in the Table below where d=D+A (2/60).

| Transition Probabilities for Distance Completed | | | | | | | |
|---|---|---|---|---|---|---|---|
| D' | −0.0201 | −0.0134 | −0.0067 | D | +0.0067 | +0.0134 | +0.0201 |
| P | 0.01 | 0.05 | 0.24 | 0.40 | 0.24 | 0.05 | 0.01 |

While the dynamics of heart rate and $T_{core}$ are complex, they have been captured to a high fidelity in physics- and physiology-based thermoregulatory models. The PSI transition probabilities were learned by Monte Carlo approximation using the SCENARIO thermoregulatory model to simulate the responses of humans under our laboratory conditions. This model requires the following class of inputs: environmental conditions, clothing insulation and vapor permeability characteristics, individual characteristics (including height, weight, and age), and work rate expressed in watts. FIG. 4 shows the transition PMF plots for PSIs 1 to 9. In FIG. 4, the current PSI state is indicated by a vertical line. The learned discrete probability distribution is shown as a grey scale heat map, white shows the highest density, black=0. Overlaid are the offset learned linear regression equations.

The linear property of the transition probabilities and developed two regression equations were used to compute the mean PSI' from current PSI and the action to be taken. One equation was for walking speeds≤4.0 mph (equation W), and one running speeds>4.0 mph (equation R). These regression lines are overlaid on the PMF in FIGS. 4A-4I. FIGS. 4A-4I illustrate the PMFs across time collapsed, because negligible difference between the PMFs at different time points was found.

$$PSI_{walk} = 0.2221S + (0.0312PSI_2 + 0.4625PSI) + 0.3365 \quad (W)$$

Where S=movement speed in miles per hour (mph).

$$PSI_{run} = 0.9012S + (0.0312PSI_2 + 0.4625PSI) - 2.2443 \quad (R)$$

These equations were used as linear Gaussian probability density functions (PDFs) with a standard deviation of 0.4 to generate a smooth transition PMF. To avoid having some probability of physiologically improbably transitions, the probability was set to zero if transition probabilities were <0.00001, and re-normalized.

The reward function provides a measure, score, or value for being in any particular state. The utility of any sequence of states can be computed from the sum of the awards. Rewards and penalties were set for each of the three study goals. The need to complete 5 miles within an hour was modeled with a large penalty for not completing the exercise within the allotted time. For the "don't get too hot" goal, exponentially increasing penalties were assigned as PSI increased above a 7.5 safety threshold. To promote completion with as low a PSI as possible, larger increasing rewards were given for lower end state PSIs. Additionally, the penalties for achieving a PSI of 10 (where HR=180 beats/min. and $T_c$=39.5° C.) were large enough that the algorithm favored stopping the individual rather than have them complete the exercise session.

An example of the reward function $R_1(s)$ for finishing the course is $$R_1(s) = \begin{Bmatrix} t < 60:0 \\ t = 60 \, \& d \geq 5:0 \\ t = 60 \, \& d < 5: -1000 \end{Bmatrix}$$

where t is time (minutes), and d is distance completed (miles).

For the "don't get too hot" goal, a PSI safety threshold of 7.5 was used as above this level individuals would transition to a "very high" thermal-work strain state, because of the risk of potential performance impairment and heat injury. The Tables below show the rewards for goals two ($R_2$) and three reward ($R_3$) respectively. In an alternative embodiment, the fineness of the final end state rewards for three reward are reduced to the 8, 8.5, 9, 9.5 and 10 PSIs. Likewise, in an alternative embodiment the rewards for $R_2$ may include additional rewards for 7.75, 8.25, 8.75, 9.25, and 9.75 PSIs where the reward is twice the next lower PSI.

| Final Rewards for $R_2(s)$ for t < 60 | | | | | | | |
|---|---|---|---|---|---|---|---|
| PSI | <7.5 | 7.5 | 8 | 8.5 | 9 | 9.5 | 10 |
| $R_2$ | 0 | −2 | −8 | −32 | −128 | −512 | −2000 |

| Final End State Rewards for $R_3(s)$ for t = 60 | | | | | | | | | |
|---|---|---|---|---|---|---|---|---|---|
| PSI | ≤8 | 8.25 | 8.5 | 8.75 | 9 | 9.25 | 9.5 | 9.75 | 10 |
| $R_3$ | 100 − (4*PSI − 2) | −4.3 | −7.6 | −10.9 | −50 | −100 | −300 | −300 | −2000 |

The $R_3$ PSI rewards were designed to promote completion of the run with the lowest possible PSI. The Final End State Rewards Table shows that finishing with a lower PSI is better than finishing with a higher PSI. However, finishing with PSIs>8 is not beneficial, and is increasingly penalized. The increasing penalties for higher and higher PSIs show the increasing risk of thermal-injury. The very large penalty of −2000 for a PSI of 10 indicates that ending here is unacceptable. It is more appropriate to stop the exercise than to push to complete the exercise.

The reward function $R_2$ Table shows that it is fine for participants to have PSIs<7.5 during the movement but at levels of PSIs≥7.5 penalties will accrue. The negative rewards for PSIs above 7.5 allow for several steps to be taken at these higher PSI's and still receive higher utility than not completing the exercise on time. However, the exponentially increasing penalties are designed to discourage straying too far into higher PSIs. These very large negative rewards at high PSIs≥9.5 are designed to indicate that stopping the exercise for health is better than completing.

A policy function (H(S)) provides an action for any given state. In the MDP definitions actions are not deterministic but have a stochastic element. This stochastic element is defined by the transition probability mass function P(S'|S, A). The utility of a policy starting in state S can be computed as the expected sum of rewards by following the policy until the end state. An MDP can be solved using dynamic programming by making use of the Bellman equation (equation below). Here the utility of being in any state can be computed as the sum of the immediate reward for being in the current state and the maximum of expected utility of the actions taken to reach each next state:

$$(s) = \max a \in (s) R(s) + \Sigma P(s'|s,a) Ut + 2(s') s'$$

An optimal solution to an MDP can be found using the computational technique of dynamic programming (Bellman, R E, Dynamic Programming, Princeton University Press, Princeton, 1957). For the pacing MDP dynamic programming recursively finds for all time points and states the pace that has the highest expected reward over the whole exercise task. The output of this computation takes the form of a look-up table which provides pacing templates with a pace for every state at every time point. This MDP dynamic programming process provides the anticipatory component to the a priori pacing template, as the pace identified in the look-up table is selected based on the overall impact to future states and the final exercise goal.

VI. EXPERIMENTATION

An experiment was run for comparing the individual using their own pacing knowledge (UNGUIDED and SELF-PACED) versus being provided pacing guidance (GUIDED). The experiment involved in total 22 individuals but only 17 individuals completed both the GUIDED and UNGUDED portions of the study and were included in the subsequent analysis.

To examine the effect of automated pacing, the overall mean, maximum, and end PSI value were compared between the GUIDED and UNGUIDED groups using a paired t-test. Results were deemed significant if p<0.05. The experiment had seventeen eligible subjects. For the GUIDED session nine subjects completed the five miles in one hour while eight subjects were guided to stop.

The volunteers participated in two treadmill exercise sessions with three goals of: 1) complete 5 miles within 60 minutes, 2) be as cool as possible at the end of the exercise, and 3) do not get too hot during the exercise. The Table below provides an overview of the seventeen volunteers who completed both sessions of the study.

|  | Males (n = 10) | Females (n = 7) | Combined (n = 17) |
|---|---|---|---|
| Age (yrs) | 22.7 ± 2.9 | 23.1 ± 3.7 | 22.9 ± 3.2 |
| Height (m) | 1.75 ± 0.07 | 1.67 ± 0.04 | 1.71 ± 0.07 |
| Weight (kg) | 70.4 ± 8.6 | 62.4 ± 6.0 | 67.13 ± 8.5 |
| % Body Fat | 11.8 ± 3.1 | 26.6 ± 4.8 | 17.8 ± 8.4 |
| Surface Area ($m^2$) | 1.85 ± 0.13 | 1.69 ± 0.08 | 1.78 ± 0.13 |
| 2 Mile Run (Min:Sec) | 14:53 ± 0:44 | 15:36 ± 0:30 | 15:11 ± 0:44 |

Body fat was estimated using the Department of Defense circumference-based equations. Body surface area was calculated using the Du Bois equation.

The first exercise session was UNGUIDED during which volunteers had to pace themselves using only distance and time for feedback, and were free to choose any pacing strategy they desired. The second session was GUIDED by an automated system (built according to at least one embodiment) that provided a treadmill speed setting every two minutes based upon the algorithmically learned pacing template, and the subject's current physiological and task completion states. If the five miles were completed prior to the 60 minutes, subjects stood until the end of the exercise time period. The exercise took place in a temperature controlled chamber where environmental conditions were set at 22° C. and 50% relative humidity. Air flow in the chambers was approximately 0.35 $ms^{-1}$. Participants exercised in their own shorts and t-shirt with the U.S. Army Physical Training (PT) uniform worn on top. The PT uniform added a significant thermal burden with a high clothing insulation factor of 1.22 CLO and low vapor permeability of 0.41 ($I_m$). Participants could drink water ad-libitum during exercise. Seventeen hours prior to the exercise the participants began a controlled caffeine free diet and engaged in only sedentary activities. Exercise began at approximately 1000 hours for all volunteers.

The subjective measures included a rating of perceived exertion (RPE) and a modified thermal sensation scale (see Table below) were recorded prior to exercise, immediately following exercise, and every 10 minutes during exercise.

Physiological Strain Index (PSI), Rating of Perceived Exertion (RPE) and Modified Thermal Sensation Scale

| PSI | | RPE | | Modified Thermal Sensation Scale | |
|---|---|---|---|---|---|
| Scale | Verbal Anchor | Scale | Verbal Anchor | Scale | Verbal Anchor |
| 0 | | 6 | No Exertion At All | −10 | Unbearably Cold |
| 1 | No/Little Strain | 7 | Extremely Light | −8 | Extremely Cold |
| 2 | | | | −6 | Very Cold |
| 3 | Low Strain | 9 | Very Light | −4 | Cold |
| 4 | | 11 | Light | −2 | Cool |
| 5 | Moderate Strain | 13 | Somewhat Hard | 0 | Comfortable |
| 6 | | 15 | Hard (Heavy) | +2 | Warm |
| 7 | High Strain | 17 | Very Hard | +4 | Hot |
| 8 | | | | +6 | Very Hot |
| 9 | Very High Strain | 19 | Extremely Hard | +8 | Extremely Hot |
| 10 | | 20 | Maximal Exertion | +10 | Unbearably Hot |

The physiological state included the physiological strain index (PSI) developed by Moran et al., which provided a measure of an individual's physiological state. The PSI scale is a weighted combination of both heart rate (HR) and body core temperature ($T_c$) and provides a simple 0-10+ scale (see Table above and prior discussion). The PSI has both a thermal component and a work rate component similar to the RPE prediction equation developed by Iyoho, MacFadden, and Ng (Iyoho A E, MacFadden L N, Ng L J. Predication of performance reduction in self-paced exercise as modulated by the rating of perceived exertion. *European Journal of Applied Physiology* 2015; 115(4):675-690).

Measurements of heart rate, body core temperature, and chest skin temperature ($T_s$) were recorded by a physiological monitoring system (Equivital EQ-02, Hidalgo Ltd., Cambridge, UK). The body core temperature measures were from a thermometer pill (Jonah Pill, Respironics, Bend, Oregon), ingested at least 12 hours prior to exercise. Skin temperatures were measured from a dermal patch placed above the right breast (Respironics, Bend, Oregon). The PSI used to determine physiological state was computed from measured heart rate, and body core temperature estimated from heart rate using the ECTemp™ algorithm as discussed above. Metabolic data were measured using an indirect whole room calorimetry (U.S. Department of Agriculture, Beltsville, Maryland).

The experiment examined the effect of automated pacing on thermal physiological state, a comparison of the overall mean, maximum, and end point $T_c$, $T_s$, HR, PSI, RPE, metabolic rate, and thermal sensation scale values between the GUIDED and SELF-PACED session using a paired t-test. Other comparisons between groups of subjects were conducted using a Student's t-test. Results were deemed significant if $p<0.05$.

The pacing template computed by the MDP was a series of lookup tables to provide the pace for each two minute segment of the exercise session based upon the distance already covered and an individual's PSI. FIG. 5A shows a selected sample of the pacing template (minutes 0, 8, 48, and 58) represented as heat maps where white to black represents a pace of 7 to 0 mph. Pace was selected based upon the time into the exercise, the distance completed (x-axis), and the subjects' current physiological strain index (PSI) (y-axis). In addition, the distance completed and PSI are shown for two subjects one who was GUIDED to complete the five miles (triangle) and one who was GUIDED to stop before completing the five miles (circle). FIG. 5B shows the template selected pace for these two subjects for each two minute period.

At various points in time after minute 0, if too little distance has been completed the template prescribes a speed of 0 mph indicating that completion is not possible under the PSI "safety" constraint, or a speed faster than maximum (7 mph) would be needed. Similarly, as PSI begins to increase above 5, prescribed pace is slowed to 0 reflecting the increasing penalties for PSI>7.5.

FIG. 5B illustrates how at time 0 both subjects are started at a similar pace, even though they have quite different starting PSI values. By minute 8, the "stopped" subject's pace is reduced due to the PSI constraints. By minute 48, the pace for both subjects is similar but the "stopped" subject still has a much higher PSI, and because of slower pacing up to this point has completed half a mile less. After minute 48, the pacing template stops this subject by providing a pace of 0 mph.

Pacing strategies varied between subjects but followed three general styles: 1) EARLY finishers that ran for the whole task and completed early; 2) STEADY pacers who ran close to the 5 mph speed necessary to finish in one hour; and 3) those that ALTERnated their pace. FIGS. 6A and 6B show the mean PSI response and pace of the three different groups (Mean speed (FIG. 6A) and PSI (FIG. 6B) for each of the three movement groups). On average the group that alternated between speeds almost keeps their PSI below the 7.5 "safety" threshold. The other two groups, however, exceed this threshold either during the mid-point or towards the end of the exercise session.

FIGS. 6A and 6B show the mean responses for movement speed and PSI for eight subjects who completed 5 miles during both GUIDED and UNGUIDED exercise sessions. Automated pacing significantly reduced the overall thermal-work strain. Mean PSI values (5.7±0.4 versus 6.8±0.8) and maximum PSI values (6.7±0.4 "High Strain", versus 9±0.9 "Very High Strain") were significantly lower in the GUIDED session. Additionally, these volunteers spent 23.8±13.2 minutes at or above a PSI value of 7.5 (high thermal-work strain) during UNGUIDED sessions but, at no time met or exceeded a PSI of 7.5 in the GUIDED session.

A comparison of the maximal and ending PSI index values for the SELF-PACED and GUIDED exercise sessions are presented in FIGS. 7A and 7B. Approximately half of the subjects were guided to stop before completing five miles (n=8) versus guided to complete the task (n=9). No significant differences were found between those guided to stop versus complete for: age, height, weight, percent body fat, or body surface area. However, those subjects the template stopped had significantly slower (p<0.05) two-mile run times (15:34±0:29 min.) versus those the template guided to completion (14:56±0:29 min.). Physiological strain index and HR were also significantly higher in those guided to stop (7.8±0.9 PSI units and 178±7 beats/min.) than those guided to completion (6.7±0.4 PSI units, and 167±6 beats/min.).

In FIG. 8, the end-point by maximum observed PSI for all subjects for both the GUIDED (squares and triangles) and SELF-PACED (X) sessions indicating those guided to completion (triangle) and those guided to stop (circle). A dashed line indicates the 7.5 PSI threshold used to provide penalties in the MDP definition.

Physiological parameters and self-reported scales for those that completed the 5 miles in both session (n=9), are shown for both the GUIDED and SELF-PACED sessions in FIGS. 9A-9F. The Table below shows the mean, maximum and end point values for the same parameters. Five mile completion times are significantly (p<0.01) faster for the SELF-PACED (52.4±6.1 min.) session compared to the GUIDED session (58.9±1.5 min.). Total energy expenditure was not significantly different between session (2.43±0.38 MJ and 2.59±0.41 MJ for SELF-PACED and GUIDED, respectively). In FIGS. 9A-9F, Mean $T_c$, $T_s$, HR, PSI, Thermal Scale, and RPE for both GUIDED and SELF-PACED sessions are shown with error bars with ±1 standard deviation.

Comparison of Physiological Parameters Between SELF-PACED and GUIDED

| | SELF-PACED | | | GUIDED | | |
|---|---|---|---|---|---|---|
| | Average | Maximum | End Point | Average | Maximum | End Point |
| $T_c$ (° C.) | 38.4 ± 0.2 | 39.0 ± 0.3 | 38.4 ± 0.6 | 38.1 ± 0.2† | 38.4 ± 0.2† | 38.1 ± 0.3 |
| $T_s$ (° C.) | 35.0 ± 0.6 | 35.7 ± 0.5 | 34.7 ± 0.5 | 34.2 ± 0.9 | 35.0 ± 0.5† | 33.3 ± 1.2† |
| HR (bpm) | 158 ± 12 | 182 ± 12 | 129 ± 27 | 150 ± 7† | 165 ± 7† | 124 ± 18 |
| PSI | 6.6 ± 0.9 | 8.7 ± 1.1 | 5.4 ± 2.3 | 5.7 ± 0.5† | 6.6 ± 0.3† | 4.6 ± 1.3 |
| Thermal | 3.0 ± 0.6 | 5.0 ± 0.9 | 2.1 ± 1.8 | 1.9 ± 1.0† | 3.2 ± 1.1† | 1.6 ± 1.7 |
| RPE | 10.6 ± 1.0 | 12.7 ± 1.2 | 6.4 ± 1.0 | 9.5 ± 1.6† | 11.3 ± 2.2 | 6.4 ± 0.7 |

† Significantly lower in the GUIDED session than the SELF-PACED p<0.05.

A system computed a priori pacing template was computed and GUIDED subjects to complete a novel thermally stressful task with significantly lower thermal-work strain. For those subjects in the GUIDED session who completed the 5 miles, average and maximal HR, $T_c$, $T_s$, and PSI were all significantly lower compared to SELF-PACED sessions. The a-priori pacing policy's effect was most striking in terms of the reduction in mean maximal values, the heart rate was lower by almost 20 beats/min., the body core temperature was lower by over 0.5° C., and PSI was lower by more than 2 points.

Two subjects obtained similar results during the SELF-PACED session compared to the GUIDED session. Both of these subjects utilized a walk/run pacing strategy switching between walking and running. One of these subjects was an experienced tri-athlete accustomed to training and competing in the heat. This subject monitored his own pulse during the exercise session. The other subjects did not do this, suggesting an unfair advantage for the automated pacing policy which was able to make use of the estimated PSI derived from real-time heart rate measurements. However, both RPE scales and thermal sensation scales were placed directly in front of the exercising subjects and ratings were requested every ten minutes during both sessions. Ratings of perceived exertion, along with the provided time and distance completed should provide adequate feedback for pacing decisions. However, for novices, it is not certain whether the feedback information could have been used in a anticipatory manner as they had no optimized template to use it against. The development of an optimal pacing template appears to take many trials and is not learned quickly. The relatively large and significant decrease in physiological strain from the SELF-PACED to the GUIDED session suggests that the a priori policy is approaching optimality for this task. This is also supported, albeit anecdotally, by the fact that the tri-athlete runner could not do better than the pacing template.

The Role of Thermal Sensation for Exercise in the Heat

While the a priori pacing policy allowed completion of the task with significantly lower physiological strain, there was only one unit reduction for average RPE from the SELF-PACED ("Light") to GUIDED ("Very Light") session. However, the mean maximal thermal sensation scale rating was significantly lower for the GUIDED (3.0 "Warm/Hot") versus SELF-PACED (5.3 "Hot/Very Hot"). The apparent greater influence of thermal sensation is supported by Schlader et al. (Schlader Z J, Simmons S E, Stannard S R, et al. Skin temperature as a thermal controller of exercise intensity. *European Journal of Applied Physiology* 2011; 111(8): 1631-1639), who observed that in the heat, skin temperature can impact pacing independently of RPE. But, the difference in $T_s$ alone does not appear to be large enough to account for the difference in thermal sensation. Gagge A P, Stolwijk J A, Saltin B., "Comfort and thermal sensations and associated physiological responses during exercise at various ambient temperatures," *Environ Res* 1969; 2(3):209-229. Both $T_c$ and $T_s$ were significantly lower in the GUIDED session suggesting, as Schlader et al. (Schlader Z J, Simmons S E, Stannard S R, et al. The independent roles of temperature and thermal perception in the control of human thermoregulatory behavior. *Physiology and Behavior* 2011; 103(2):217-224) observed, that the thermal sensation scale ratings are affected by a combination of both $T_c$ and $T_s$. For this thermally-stressful task the thermal sensation scale is more sensitive to changes in $T_c$ and $T_s$ than RPE. In this context the thermal sensation scale seems to reflect the additional information necessary to control pace.

This study demonstrated that a machine computed a priori pacing template paced subjects to complete a novel thermally-challenging task with significantly less thermal-work strain compared to self-pacing. The method of describing an exercise task and physiological constraints in terms of a dynamical system can be applied to other time-constrained physical tasks. For exercise events where pacing is much more dependent on body core temperature (e.g., 30 to 120 minutes), the present approach allows an a priori pacing template to be developed that can be used with heart rate monitoring feedback. The results indicate that an a priori pacing template with heart rate feedback would have the following advantages: (1) it would adapt the pace to individual fitness, (2) it would allow a novice to quickly adopt a pacing strategy better than their own; and (3) it would allow an expert to adapt more quickly to an optimized pacing strategy in hot environmental conditions.

As will be appreciated by one skilled in the art based on this disclosure, aspects of the present invention may be embodied as a system, method or computer program product. Accordingly, aspects of the present invention may take the form of an entirely hardware embodiment, a processor operating with software embodiment (including firmware, resident software, micro-code, etc.) or an embodiment combining software and hardware aspects that may all generally be referred to herein as a "circuit," "module" or "system."

Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this disclosure, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Computer program code for carrying out operations for aspects of the present invention may be written in any combination of one or more programming languages, including an object oriented programming language such as Xcode®, Ruby, Python®, Java™, Smalltalk, Objective C, C++, C#, Transact-SQL, XML, or the like and conventional procedural programming languages, such as the "C" programming language or similar programming languages. The program code may execute entirely on the user's computer (or other computing device worn by the individual), partly on the user's computer, as a stand-alone software package, partly on the user's computer and partly on a remote computer or entirely on the remote computer or server. In the latter scenario, the remote computer may be connected to the user's computer through any type of network, including Bluetooth®, a local area network (LAN) or a wide area network (WAN), or the connection may be made to an external computer (for example, through the Internet using an Internet Service Provider).

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Referring now to FIG. 10, a representative hardware environment for practicing at least one embodiment of the invention is depicted. This schematic drawing illustrates a hardware configuration of an information handling/computer system in accordance with at least one embodiment of the invention. As should be appreciated by one of ordinary skill in the art, the computer system may be implemented on a smartphone or computing device worn by the individual). The system comprises at least one processor or central processing unit(s) (CPU) 1010. The CPU(s) 1010 are interconnected with system bus 1012 to various devices such as a random access memory (RAM) 1014, read-only memory (ROM) 1016, and an input/output (I/O) adapter 1018. The I/O adapter 1018 can connect to peripheral devices or other program storage devices that are readable by the system. The system can read the inventive instructions on the program storage devices and follow these instructions to execute the methodology of at least one embodiment of the invention. The system further includes a user interface adapter 1019 that connects a keyboard or other button interface 1015, speaker 1024, microphone 1022, and/or other user interface devices such as a touch screen device (not shown) to the bus 1012 to gather user input. Additionally, a communication adapter 1020 connects the bus 1012 to a data processing network 1025, and a display adapter 1021 connects (either wirelessly or wired) the bus 1012 to a display device 1023 which may be embodied as an output device such as a monitor, printer, or transmitter, for example.

The flowchart and block diagrams in the Figures illustrate the architecture, functionality, and operation of possible implementations of systems, methods and computer program products according to various embodiments of the present invention. In this regard, each block in the flowchart or block diagrams may represent a module, circuit, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

Although the present invention has been described in terms of particular example embodiments, it is not limited to those embodiments. The embodiments, examples, and modifications which would still be encompassed by the invention may be made by those skilled in the art, particularly in light of the foregoing teachings.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

The use of "of at least one of" in the claims is to be read as alternatives and not to require inclusion of all of the listed items.

VII. INDUSTRIAL APPLICABILITY

In at least one embodiment, the system and/or the method will enable practical real-time monitoring systems that can improve human health through preventing thermal injury and use reinforcement learning to improve the physical performance of novice athletes and regular individuals.

The invention claimed is:

1. A system for providing pacing guidance to an individual while performing an activity, the system comprising:
   a heart rate monitor;
   an activity completion module configured to determine a level of the activity currently being performed that has been completed by the individual;
   a memory storing
      a plurality of pacing templates configured for at least the activity being performed by the individual and different activity completion levels of the activity being performed by the individual, and
      a look-up table having entries for the plurality of pacing templates;
   an output device;
   a processor in communication with said heart rate monitor, said memory, said activity completion module, and said output device, said processor configured to
      receive a heart rate signal from said heart rate monitor where the heart rate signal represents a heart rate,
      receive a signal from said activity completion module representing the amount of the activity currently completed by the individual,
      calculate a physiological strain index (PSI) where the heart rate is an input into the PSI,
      selecting one pacing template based on the PSI and the amount of the activity currently completed using the look-up table in said memory, and
      outputting information in said one pacing template to said output device, and
   wherein the pacing templates include different levels at which to perform the activity.

2. The system according to claim 1, wherein the plurality of templates are configured based on predetermined goals to allow completion of the task within an allotted time with the lowest PSI at an end of the activity being performed.

3. The system according to claim 1, further comprising:
   a clock in communication with said processor; and
   wherein said processor is further configured to
      receive a time from said clock, and
      select one pacing template based on the PSI, the time, and the amount of the activity currently completed using the look-up table in said memory.

4. The system according to claim 3, further comprising:
   a skin temperature sensor in communication with said processor; and
   wherein the PSI is an adaptive physiological strain index (aPSI), and
   said processor is further configured to
      receive a temperature signal from said skin temperature sensor representing skin temperature,
      calculate the aPSI using the heart rate, a core temperature estimated based on the heart rate, a critical core temperature based on an adaptive skin-core temperature gradient, a predetermined critical heart rate, a resting heart rate, and a resting core temperature, and
      select one pacing template based on the aPSI, the time, and the amount of the activity completed using the look-up table in said memory.

5. The system according to claim 1, wherein said heart rate monitor is selected from a group consisting of a heart rate sensor attached to the subject person, a processor for receiving EKG signals from electrodes attached to the person, a pulse oximeter sensor, and a processor for receiving a ballistic-cardiogram signal.

6. The system according to claim 1, further comprising an input for receiving identification of the activity being performed by the individual.

7. The system according to claim 6, wherein said plurality of pacing templates includes templates for different activities selected from a group consisting of running, cycling, hiking, swimming, climbing, walking, cardiovascular exercising, cleaning, vehicle washing, and skating.

8. The system according to claim 1, wherein said processor selects a pacing template at predetermined time intervals or at predetermined time intervals based on a percentage of the activity currently completed.

9. The system according to claim 1, further comprising at least one atmospheric sensor in communication with said processor, said at least one atmospheric sensor including a temperature sensor or a humidity sensor; and
   wherein said processor uses a signal received from said at least one atmospheric sensor in selecting a subset of pacing templates, and
   wherein selecting one pacing template based on the PSI and the amount of the activity completed using the look-up table in said memory selects the one pacing template from the selected subset of pacing templates.

10. The system according to claim 1, further comprising a clothing module configured to receive input regarding the clothing being worn by the individual, and
   wherein said processor uses the clothing input in selecting a subset of pacing templates, and
   wherein selecting one pacing template based on the PSI and the amount of the activity completed using the look-up table in said memory selects the one pacing template from the selected subset of pacing templates.

11. A method for recommending by a processor a pace to an individual based on an activity and physiological state of the individual, said method comprising at predetermined intervals:
   receiving a strain signal for the individual from a physiological strain state (PSS) module, or receiving a heart rate for the individual from a heart rate monitor attached to the individual;
   receiving a representation of an amount of the activity currently completed by the individual;
   determining a physiological strain index (PSI) where the received strain signal or the received heart rate is an input for the PSI;
   selecting a pacing template from a plurality of pacing templates contained in storage using the PSI and the representation of the amount of the activity currently completed; and
   providing pacing information based on the selected pacing templates to the individual to allow the individual to adjust the pace at which the activity is being performed.

12. The method according to claim 11, further comprising:
   receiving a time signal from a clock; and
   wherein selecting the pacing template uses the PSI, the received time signal, and the representation of the amount of the activity completed to select a pacing template from a plurality of pacing templates contained in storage.

13. The method according to claim 12, further comprising:
   receiving at least one atmospheric condition from an atmospheric sensor; and
   selecting a subset of pacing templates from which the processor selects the pacing template based on the PSI, the received time signal and the representation of the amount of the activity completed using the at least one atmospheric condition.

14. The method according to claim 11, further comprising:
   receiving a body core temperature from a temperature sensor internal to the individual; and
   wherein the strain signal provided by the PSS module is determined based on the body core temperature and the received strain signal or based on the body core temperature and the received heart rate.

15. The method according to claim 11, wherein the activity is selected from a group consisting of a run, a bicycle ride, a hike, a swim, a climb, a walk, a cardiovascular workout, cleaning, washing a vehicle, skating, and any combination of these activities.

16. The method according to claim 11, further comprising transmitting the pace information and physiological information to an external device collecting information from a plurality of individuals.

17. The method according to claim 11, further comprising receiving an identification of the clothing being worn by the individual and/or the activity being performed by the individual.

18. The method according to claim 11, wherein the activity is running and/or walking.

19. The method according to claim 11, wherein the plurality of pacing templates includes templates for no movement and speeds between 2 mph to 7 mph and the level of completion is based on distance covered.

20. The method according to claim 11, further comprising determining any applicable penalty for the individual based on PSI, and
   wherein the penalty is used to select the pacing template.

* * * * *